(12) United States Patent
Renner et al.

(10) Patent No.: US 7,714,113 B2
(45) Date of Patent: May 11, 2010

(54) FUSION PROTEINS OF HUMANIZED G250 SPECIFIC ANTIBODIES AND USES THEREOF

(75) Inventors: Christoph Renner, Homburg (DE); Andrew Scott, Parkville (AU)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 10/504,389

(22) PCT Filed: Feb. 12, 2003

(86) PCT No.: PCT/US03/04243

§ 371 (c)(1), (2), (4) Date: Apr. 15, 2005

(87) PCT Pub. No.: WO03/068924

PCT Pub. Date: Aug. 21, 2003

(65) Prior Publication Data

US 2006/0045876 A1    Mar. 2, 2006

(51) Int. Cl.
*C12P 21/08* (2006.01)
(52) U.S. Cl. .................. 530/391.7; 530/350; 530/387.3; 435/320.1; 435/326; 536/23.53
(58) Field of Classification Search ............. 530/387.3, 530/391.7, 350; 536/23.53; 435/320.1, 325, 435/326
See application file for complete search history.

(56) References Cited

U.S. PATENT DOCUMENTS 5,955,075 A * 9/1999 Zavada et al.

OTHER PUBLICATIONS

Xiang et al. Journal of Biotechnology, 53:3-12, Feb. 28, 1997.*
Kamali-Sarcestani et al. (Pathology Oncology Research, 11(2):99-102, 2005).*
Jones (Pharmacogenomics Journal, 1:126-134, 2001).*
Tosatto et al (Current Pharmaceutical Design, 12:2067-2086, 2006).*
Pennica et al (JBC, 267(29):21172-21178, 1992).*
Antibody Engineering, (Edited by McCafferty et al, pp. 269-272, 1996).*
Luiten et al (Human antibodies, 8(4):169-180, 1997).*
Steffens et al (Cancer Research, 59:1615-1619, 1999).*
Hoogenboom et al (Molecular Immunology, 28:9:1027-1037, 1991).*
Divgi et al. (Clin Cancer Res, Nov. 1998;4(11):2729-39).*
Van Dijk et al (Int. J Cancer, 56:262-268, 1994).*
Rosenblum et al (Int J Cancer, 88:267-273, 2000).*
Kranenborg et al (Int J Cancer, 75:74-80, 1998).*
Tabata et al (J Cont. Release, 59:187-196, 1999).*
Weijtens et al (Gene Ther. Jan. 2000;7(1):35-42).*
Skolnick et al. (Trends in Biotechnology 2000; 18: 34-39).*
McCarron et al (Mol. Int., 5(6):368-380, 2005).*
Yang, et al., "A Genetically Engineered Single-Chain FV/TNF Molecule Possesses the Anti-Tumor Immunoreactivity of FV as Well as the Cytotoxic Activity of Tumor Necrosis Factor," Molecular Immunology, Elmsford, NY, US, vol. 32, No. 12, pp. 873-881 (Aug. 1, 1995).
Steffens, et al., "Phase I Radioimmunotherapy of Metastatic Renal Cell Carcinoma With 131I-Labeled Chimeric Monoclonal Antibody G250," Clinical Cancer Research, The American Association for Cancer Research, US, vol. 5, pp. 3268s-3274s (Oct. 1999).

* cited by examiner

*Primary Examiner*—Stephen L Rawlings
*Assistant Examiner*—Brad Duffy
(74) *Attorney, Agent, or Firm*—Fulbright & Jaworski LLP

(57) ABSTRACT

Chimeric antibodies, as well as fusion proteins which comprise chimeric antibodies, are disclosed. The antibodies bind to GM-CSF, CD-30, and G250 antigen. The fusion proteins include biologically active portions of tumor necrosis factor, or full length tumor necrosis factor. Expression vectors adapted for production of the antibodies, as well as methods for manufacturing these, are also disclosed.

9 Claims, 6 Drawing Sheets

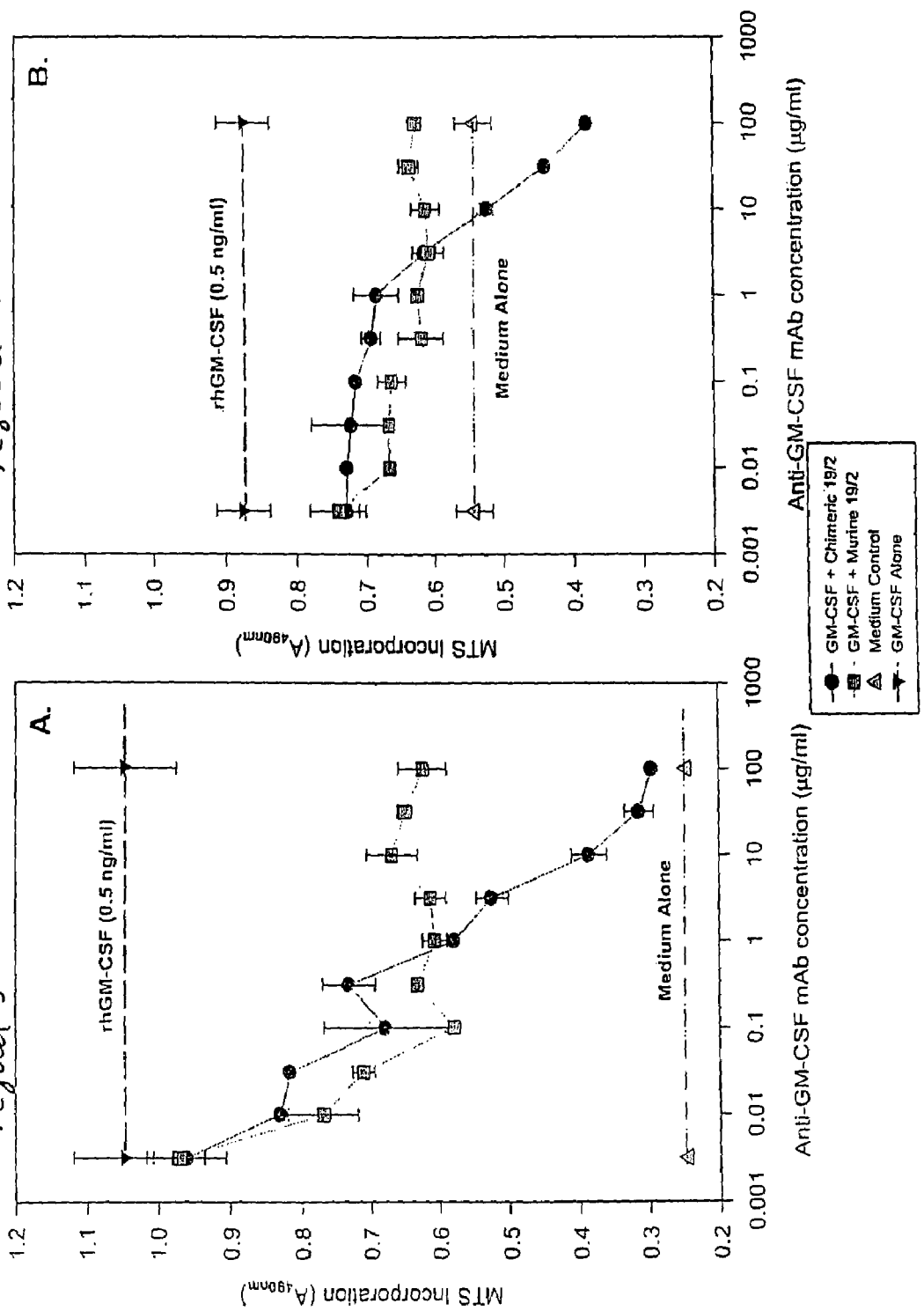

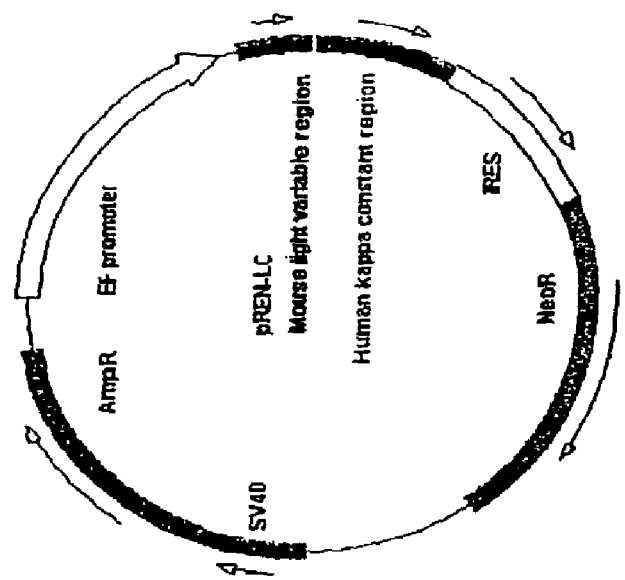
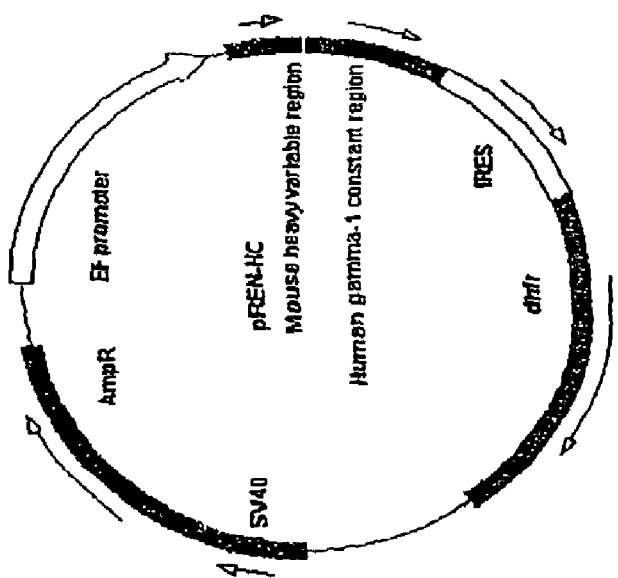
FIGURE 7

```
                       SEQUENCE LISTING

<160> NUMBER OF SEQ ID NOS: 56

<210> SEQ ID NO 1
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 1
atgaaatgca gctgggtcat sttcttc                                         27

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 2
atgggatgga gctratcats ytctt                                           25

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 3
atgaagwtgt ggttaaactg ggttttt                                         27

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 4
atgractttg wytcagcttg rttt                                            24

<210> SEQ ID NO 5
```

```
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 5
atggactcca ggctcaamag ttttcctt                                   28

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 6
atggctgtcy trgsgctrct cttctgc                                    27

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 7
atggratgga gckggrtctt tmtctt                                     26

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 8
atgagagtgc tgattctttt gtg                                        23

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 9
atggmttggg tgtggamctt gctattcctg                                 30

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 10
atgggcagac ttacattctc attcctg                                    27

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 11
```

-continued atggattttg ggctgatttt ttttattg     28

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 12
atgatggtgt aagtcttct gtacctg     27

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 13
atgaagttgc ctgttaggct gttggtgctg     30

<210> SEQ ID NO 14
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 14
atggagwcag acacactcct gytatgggt     29

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 15
atgagtgtgc tcactcaggt cctggsgttg     30

<210> SEQ ID NO 16
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 16
atgaggrccc ctgctcagwt tyttggmwtc ttg     33

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 17
atggatttwc aggtgcagat twtcagcttc     30

<210> SEQ ID NO 18
<211> LENGTH: 27
<212> TYPE: DNA

```
<213> ORGANISM: Artificial Sequence
<220> FEATURE:
<223> OTHER INFORMATION: Oligonucleotide primer

<400> SEQUENCE: 18
atgaggtkcy ytgytsagyt yctgrgg                                              27

<210> SEQ ID NO 19
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 19
atgggcwtca agatggagtc acakwyycwg g                                         31

<210> SEQ ID NO 20
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 20 atgtgggay ctktttycmm tttttcaatt g                                          31

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 21
atggtrtccw casctcagtt ccttg                                                25

<210> SEQ ID NO 22
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 22
atgtatatat gtttgttgtc tatttct                                              27

<210> SEQ ID NO 23
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 23
atggaagccc cagctcagct tctcttcc                                             28

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 24
atgaagtttc cttctcaact tctgctc                                              27
```

<210> SEQ ID NO 25
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 25
tggatggtgg gaagatg                                                    17

<210> SEQ ID NO 26
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 26
ccagtggata gacagatg                                                   18

<210> SEQ ID NO 27
<211> LENGTH: 456
<212> TYPE: DNA
<213> ORGANISM: Mus musculus
<220> FEATURE:
<223> OTHER INFORMATION: murine 19/2 heavy chain variable region

<400> SEQUENCE: 27
atggagctga tcatgctctt cctcctgtca ggaactgcag gcgtccactc                50
tgaggtccag cttcagcagt caggacctga actggtgaaa cctggggcct               100
cagtgaagat atcctgcaag gcttctggat acactttcac tgactacaac               150
atacactggg tgaaacagag ccatggaaag agccttgact ggattggata               200
tattgctcct acagtggtg gtactggtta caaccaggag ttcaagaaca                250
gggccacatt gactgtagac aaatcctcca gcacagccta catggagctc               300
cgcagtctga catctgatga ctctgcagtc tattactgtg ctagacgaga               350
ccgtttccct tattactttg actactgggg ccaaggcacc cctctcacag               400
tctcctcagc caaaacgaca ccccatctg tctatccact ggcaagggcg                450
aattcc                                                               456

<210> SEQ ID NO 28
<211> LENGTH: 139
<212> TYPE: PRT
<213> ORGANISM: Mus musculus
<220> FEATURE:
<223> OTHER INFORMATION: amino acid sequence for murine 19/2 heavy chain
      variable region

<400> SEQUENCE: 28

Met Glu Leu Ile Met Leu Phe Leu Leu Ser Gly Thr Ala Gly Val His
                 5                  10                  15

Ser Glu Val Gln Leu Gln Gln Ser Gly Pro Glu Leu Val Lys Pro Gly
            20                  25                  30

Ala Ser Val Lys Ile Ser Cys Lys Ala Ser Gly Tyr Thr Phe Thr Asp
        35                  40                  45

Tyr Asn Ile His Trp Val Lys Gln Ser His Gly Lys Ser Leu Asp Trp
    50                  55                  60

Ile Gly Tyr Ile Ala Pro Tyr Ser Gly Gly Thr Gly Tyr Asn Gln Glu

```
                65                  70                  75                  80
Phe Lys Asn Arg Ala Thr Leu Thr Val Asp Lys Ser Ser Thr Ala
                85                  90                  95

Tyr Met Glu Leu Arg Ser Leu Thr Ser Asp Ser Ala Val Tyr Tyr
                100                 105                 110

Cys Ala Arg Arg Asp Arg Phe Pro Tyr Phe Asp Tyr Trp Gly Gln Gly
                115                 120                 125

Thr Thr Leu Arg Val Ser Ser Val Ser Gly Ser
            130                 135

<210> SEQ ID NO 29
<211> LENGTH: 450
<212> TYPE: DNA
<213> ORGANISM: Mus musculus
<220> FEATURE:
<223> OTHER INFORMATION: murine 19/2 light chain variable region

<400> SEQUENCE: 29
atgggcttca agatggagtc acagatccag gtctttgtat acatgttgct         50
gtggttgtct ggtgttgatg gagacattgt gatgatccag tctcaaaaat        100
tcgtatccac atcagtagga cagggtca atatcacctg caaggccagt          150
cagaatgtgg gaagtaatgt agcctggttg caacagaaac ctggacaatc        200
tcctaaaacg ctgatttact cggcatcgta ccggtccggt cgagtccctg        250
atcgcttcac aggcagtgga tctggaacag atttcattct taccatcact        300
actgtgcagt ctgaagactt ggcagaatat ttctgtcagc aatttaacag        350
gtctcctctc acgttcggtt ctgggaccaa gttggaactg aaacgggctg        400
atgctgcacc aactgtatcc atcttcccac catccagtaa gggcgaattc        450

<210> SEQ ID NO 30
<211> LENGTH: 150
<212> TYPE: PRT
<213> ORGANISM: Mus musculus
<220> FEATURE:
<223> OTHER INFORMATION: amino acid sequence for murine 19/2 light chain
      variable region

<400> SEQUENCE: 30

Met Gly Phe Lys Met Glu Ser Gln Ile Gln Val Phe Val Tyr Met Leu
                5                   10                  15

Leu Trp Leu Ser Gly Val Asp Gly Asp Ile Val Met Ile Gln Ser Gln
                20                  25                  30

Lys Phe Val Ser Thr Ser Val Gly Asp Arg Val Asn Ile Thr Cys Lys
                35                  40                  45

Ala Ser Gln Asn Val Gly Ser Asn Val Ala Trp Leu Gln Gln Lys Pro
        50                  55                  60

Gly Gln Ser Pro Lys Thr Leu Ile Tyr Ser Ala Ser Tyr Arg Ser Gly
65                  70                  75                  80

Arg Val Pro Asp Arg Phe Thr Gly Ser Gly Ser Gly Thr Asp Phe Ile
                85                  90                  95

Leu Thr Ile Thr Thr Val Gln Ser Glu Asp Leu Ala Glu Tyr Phe Cys
                100                 105                 110

Gln Gln Phe Asn Arg Ser Pro Leu Thr Phe Gly Ser Gly Thr Lys Leu
                115                 120                 125

Glu Leu Lys Arg Ala Asp Ala Ala Pro Thr Val Ser Ile Phe Pro Pro
        130                 135                 140
```

Ser Ser Lys Gly Glu Phe
145                 150

<210> SEQ ID NO 31
<211> LENGTH: 41
<212> TYPE: DNA
<213> ORGANISM: Artificial Sequence
<220> FEATURE:
<223> OTHER INFORMATION: primer used for the construction of the
      chimeric 19/2 light chain

<400> SEQUENCE: 31 catgttताaa cgccgccacc atgggcttca agatggagtc a                    41

<210> SEQ ID NO 32
<211> LENGTH: 38
<212> TYPE: DNA
<213> ORGANISM: Artificial Sequence
<220> FEATURE:
<223> OTHER INFORMATION: primer used for the construction of the
      chimeric 19/2 light chain

<400> SEQUENCE: 32
agaggatcca ctcacgtttc agttccactt ggtcccag                        38

<210> SEQ ID NO 33
<211> LENGTH: 43
<212> TYPE: DNA
<213> ORGANISM: Artificial Sequence
<220> FEATURE:
<223> OTHER INFORMATION: primer used for the construction of the
      chimeric 19/2 heavy chain

<400> SEQUENCE: 33
catgtttaaa cgccgccacc atggagctga tcatgctctt cct                  43

<210> SEQ ID NO 34
<211> LENGTH: 37
<212> TYPE: DNA
<213> ORGANISM: Artificial Sequence
<220> FEATURE:
<223> OTHER INFORMATION: primer used for the construction of the
      chimeric 19/2 heavy chain

<400> SEQUENCE: 34
agaggatcca ctcacctgag gagactctga gagtggt                         37

<210> SEQ ID NO 35
<211> LENGTH: 6159
<212> TYPE: DNA
<213> ORGANISM: Artificial Sequence
<220> FEATURE:
<223> OTHER INFORMATION: pREN 19/2 LC Neo Vector

<400> SEQUENCE: 35
ctcgagagcg ggcagtgagc gcaacgcaat taatgtgagt tagctcactc           50
attaggcacc ccaggcttta cactttatgc tcccggctcg tatgttgtgt          100
ggagattgtg agcggataac aatttcacac agaattcgtg aggctccggt          150
gcccgtcagt gggcagagcg cacatcgccc acagtccccg agaagttggg          200
gggaggggtc ggcaattgaa ccggtgccta gagaaggtgg cgcggggtaa          250
actgggaaag tgatgtcgtg tactggctcc gcctttttcc cgagggtggg          300
ggagaaccgt atataagtgc agtagtcgcc gtgaacgttc tttttcgcaa          350

-continued

```
cgggtttgcc gccagaacac aggtaagtgc cgtgtgtggt tcccgcgggc        400
ctggcctctt tacgggttat ggcccttgcg tgccttgaat tacttccacg        450
cccctggctg cagtacgtga ttcttgatcc cgagcttcgg gttggaagtg        500
ggtgggagag ttcgaggcct tgcgcttaag gagcccttc gcctcgtgct         550
tgagttgagg cctggcctgg gcgctggggc cgccgcgtgc gaatctggtg        600
gcaccttcgc gcctgtctcg ctgctttcga taagtctcta gccatttaaa       650
attttgatg acctgctgcg acgcttttt tctggcaaga tagtcttgta         700
aatgcgggcc aagatctgca cactggtatt tcggttttg gggccgcggg        750
cggcgacggg gcccgtgcgt cccagcgcac atgttcggcg aggcggggcc        800
tgcgagcgcg gccaccgaga atcggacggg ggtagtctca agctggccgg       850
cctgctctgg tgcctggcct cgcgccgccg tgtatcgccc cgccctgggc       900
ggcaaggctg gcccggtcgg caccagttgc gtgagcggaa agatggccgc       950
ttcccggccc tgctgcaggg agctcaaaat ggaggacgcg cgcgctcggga     1000
gagcgggcgg gtgagtcacc cacacaaagg aaaagggcct ttccgtcctc      1050
agccgtcgct tcatgtgact ccacggagta ccggcgccg tccaggcacc      1100
tcgattagtt ctcgagcttt tggagtacgt cgtctttagg ttgggggag      1150
gggttttatg cgatggagtt tccccacact gagtgggtgg agactgaagt      1200
taggccagct tggcacttga tgtaattctc cttggaattt gccctttttg     1250
agtttggatc ttggttcatt ctcaagcctc agacagtggt tcaaagtttt     1300
tttcttccat ttcaggtgta cgcgtctcgg gaagctttag tttaaacgcc     1350
gccacc atg ggc ttc aag atg gag tca cag atc cag gtc ttt      1392
        Met Gly Phe Lys Met Glu Ser Gln Ile Gln Val Phe
                     5                  10
gta tac atg ttg ctg tgg ttg tct ggt gtt gat gga gac att     1434
Val Tyr Met Leu Leu Trp Leu Ser Gly Val Asp Gly Asp Ile
        15                  20                  25
gtg atg atc cag tct caa aaa ttc gta tcc aca tca gta gga     1476
Val Met Ile Gln Ser Gln Lys Phe Val Ser Thr Ser Val Gly
            30                  35                  40
gac agg gtc aat atc acc tgc aag gcc agt cag aat gtg gga     1518
Asp Arg Val Asn Ile Thr Cys Lys Ala Ser Gln Asn Val Gly
                45                  50
agt aat gta gcc tgg ttg caa cag aaa cct gga caa tct cct     1560
Ser Asn Val Ala Trp Leu Gln Gln Lys Pro Gly Gln Ser Pro
55                  60                  65
aaa acg ctg att tac tcg gca tcg tac cgg tcc ggt cga gtc     1602
Lys Thr Leu Ile Tyr Ser Ala Ser Tyr Arg Ser Gly Arg Val
        70                  75                  80
cct gat cgc ttc aca ggc agt gga tct gga aca gat ttc att     1644
Pro Asp Arg Phe Thr Gly Ser Gly Ser Gly Thr Asp Phe Ile
            85                  90                  95
ctt acc atc act act gtg cag tct gaa gac ttg gca gaa tat     1686
Leu Thr Ile Thr Thr Val Gln Ser Glu Asp Leu Ala Glu Tyr
                100                 105                 110
ttc tgt cag caa ttt aac agg tct cct ctc acg ttc ggt tct     1728
Phe Cys Gln Gln Phe Asn Arg Ser Pro Leu Thr Phe Gly Ser
                    115                 120
ggg acc aag ttg gaa ctg aaa cgt gagtggatcc atctgggata       1772
Gly Thr Lys Leu Glu Leu Lys Arg
```

-continued

```
                125                 130
agcatgctgt tttctgtctg tccctaacat gccctgtgat tatgcgcaaa            1822
caacacaccc aagggcagaa ctttgttact taaacaccat cctgtttgct            1872
tctttcctca gga act gtg gct gca cca tct gtc ttc atc ttc            1915
            Thr Val Ala Ala Pro Ser Val Phe Ile Phe
                    135                 140 ccg cca tct gat gag cag ttg aaa tct gga act gcc tct gtt           1957
Pro Pro Ser Asp Glu Gln Leu Lys Ser Gly Thr Ala Ser Val
        145                 150                 155 gtg tgc ctg ctg aat aac ttc tat ccc aga gag gcc aaa gta           1999
Val Cys Leu Leu Asn Asn Phe Tyr Pro Arg Glu Ala Lys Val
            160                 165                 170 cag tgg aag gtg gat aac gcc ctc caa tcg ggt aac tcc cag           2041
Gln Trp Lys Val Asp Asn Ala Leu Gln Ser Gly Asn Ser Gln
                175                 180 gag agt gtc aca gag cag gac agc aag gac agc acc tac agc           2083
Glu Ser Val Thr Glu Gln Asp Ser Lys Asp Ser Thr Tyr Ser
185                 190                 195 ctc agc agc acc ctg acg ctg agc aaa gca gac tac gag aaa           2125
Leu Ser Ser Thr Leu Thr Leu Ser Lys Ala Asp Tyr Glu Lys
        200                 205                 210 cac aaa gtc tac gcc tgc gaa gtc acc cat cag ggc ctg agc           2167
His Lys Val Tyr Ala Cys Glu Val Thr His Gln Gly Leu Ser
            215                 220                 225 tcg ccc gtc aca aag agc ttc aac agg gga gag tgt tga               2206
Ser Pro Val Thr Lys Ser Phe Asn Arg Gly Glu Cys
                230                 235 gctagaacta actaactaag ctagcaacgg tttccctcta gcgggatcaa            2256
ttccgccccc ccccctaac gttactggcc gaagccgctt ggaataaggc             2306
cggtgtgcgt ttgtctatat gttatttttcc accatattgc cgtcttttgg           2356
caatgtgagg gcccggaaac ctggccctgt cttcttgacg agcattccta            2406
ggggtctttc ccctctcgcc aaaggaatgc aaggtctgtt gaatgtcgtg            2456
aaggaagcag ttcctctgga agcttcttga agacaaacaa cgtctgtagc            2506 gacccttgc aggcagcgga accccccacc tggcgacagg tgcctctgcg             2556
gccaaaagcc acgtgtataa gatacacctg caaaggcggc acaaccccag            2606
tgccacgttg tgagttggat agttgtggaa agagtcaaat ggctctcctc            2656
aagcgtattc aacaaggggc tgaaggatgc ccagaaggta ccccattgta            2706
tgggatctga tctggggcct cggtgcacat gctttacgtg tgtttagtcg            2756
aggttaaaaa acgtctaggc cccccgaacc acggggacgt ggttttcctt            2806
tgaaaaacac gataatacca tggttgaaca agatggattg cacgcaggtt            2856
ctccggccgc ttgggtggag aggctattcg gctatgactg ggcacaacag            2906
acaatcggct gctctgatgc cgccgtgttc cggctgtcag cgcaggggcg            2956
cccggttctt tttgtcaaga ccgacctgtc cggtgccctg aatgaactgc            3006
aggacgaggc agcgcggcta tcgtggctgg ccacgacggg cgttccttgc            3056
gcagctgtgc tcgacgttgt cactgaagcg ggaagggact ggctgctatt            3106
gggcgaagtg ccggggcagg atctcctgtc atctcacctt gctcctgccg            3156
agaaagtatc catcatggct gatgcaatgc ggcggctgca tacgcttgat            3206
ccggctacct gcccattcga ccaccaagcg aaacatcgca tcgagcgagc            3256
```

```
acgtactcgg atggaagccg gtcttgtcga tcaggatgat ctggacgaag      3306
agcatcaggg gctcgcgcca gccgaactgt tcgccaggct caaggcgcgc      3356
atgcccgacg gcgaggatct cgtcgtgacc catggcgatg cctgcttgcc      3406
gaatatcatg gtggaaaatg gccgcttttc tggattcatc gactgtggcc      3456
ggctgggtgt ggcggaccgc tatcaggaca tagcgttggc tacccgtgat      3506
attgctgaag agcttggcgg cgaatgggct gaccgcttcc tcgtgcttta      3556
cggtatcgcc gctcccgatt cgcagcgcat cgccttctat cgccttcttg      3606
acgagttctt ctgagtcgat cgacctggcg taatagcgaa gaggcccgca      3656
ccgatcgccc ttcccaacag ttgcgcagcc tgaatggcga atgggacgcg      3706
ccctgtagcg gcgcattaag cgcggcgggt gtggtggtta cgcgcagcgt      3756
gaccgctaca cttgccagcg ccctagcgcc cgctcctttc gctttcttcc      3806
cttcctttct cgccacgttc gccggctttc cccgtcaagc tctaaatcgg      3856
gggctccctt tagggttccg atttagtgct ttacggcacc tcgaccccaa      3906
aaaacttgat tagggtgatg gttcacgtag tgggccatcg ccctgataga      3956
cggttttttcg cctttgacgt tggagtccac gttctttaat agtggactct     4006
tgttccaaac tggaacaaca ctcaaccctaa tctcggtcta tttataaggg      4056
attttgccga tttcggccta ttggttaaaa aatgagctga tttaacaaaa      4106
tttaacgcga attttaacaa aatattaacg cttacaattt aggtggcact      4156
tttcggggaa atgtgcgcgg aacccctata tttgtttatt tttctaaata      4206
cattcaaata tgtatccgct catgagacaa taaccctgat aaatgcttca      4256
ataatattga aaaggaaga gtatgagtat tcaacatttc cgtgtcgccc       4306
ttattccctt ttttgcggca ttttgcctta ctgttttttgc tcacccagaa     4356
acgctggtga agtaaaaga tgctgaagat cagttgggtg cacgagtggg       4406
ttacatcgaa ctggatctca acagcggtaa gatccttgag agttttcgcc      4456
ccgaagaacg ttttccaatg atgagcactt ttaaagttct gctatgtggc      4506
gcggtattat cccgtattga cgccgggcaa gagcaactcg gtcgccgcat      4556
acactattct cagaatgact tggttgagta ctcaccagtc acagaaaagc      4606
atattacgga tggcatgaca gtaagagaat tatgcagtgc tgccataacc      4656
atgagtgata acactgcggc caacttactt ctgacaacga tcggaggacc      4706
gaaggagcta accgcttttt tgcacaacat gggggatcat gtaactcgcc      4756
ttgatcgttg ggaaccggag ctgaatgaag ccataccaaa cgacgagcgt      4806
gacaccacga tgcctgtagc aatggcaaca acgttgcgca aactattaac      4856
tggcgaacta cttactctag cttcccggca acaattaata gactggatgg      4906
aggcggataa agttgcagga ccacttctgc gctcggccct tccggctggc      4956
tggtttattg ctgataaatc tggagccggt gagcgtgggt ctcgcggtat      5006
cattgcagca ctggggccag atggtaagcc ctcccgtatc gtagttatct      5056
acacgacggg gagtcaggca actatggatg aacgaaatag acagatcgct      5106
gagataggtg cctcactgat taagcattgg taactgtcag accaagttta      5156
ctcatatata ctttagattg atttaaaact tcatttttaa tttaaaagga      5206
```

-continued

| | |
|---|---|
| tctaggtgaa gatccttttt gataatctca tgaccaaaat cccttaacgt | 5256 |
| gagttttcgt tccactgagc gtcagacccc gtagaaaaga tcaaaggatg | 5306 |
| ttcttgagat cctttttttc tgcacgtaat ctgctgcttg caaacaaaaa | 5356 |
| accaccgcta ccagcggtgg tttgtttgcc ggatcaagag ctaccaactc | 5406 |
| tttttccgaa ggtaactggc ttcagcagag cgcagatacc aaatactgtc | 5456 |
| cttctagtgt agccgtagtt aggccaccac ttcaagaact ctgtagcacc | 5506 |
| gcctacatac ctcgctctgc taatcctgtt accagtggct gctgccagtg | 5556 |
| gcgataagtc gtgtcttacc gggttggact caagacgata gttaccggat | 5606 |
| aaggcgcagc ggtcgggctg aacggggggt tcgtgcacac agcccagctt | 5656 |
| ggagcgaacg acctacaccg aactgagata cctacagcgt gagctatgag | 5706 |
| aaagcgccac gcttcccgaa gggagaaagg cggacaggta tccggtaagc | 5756 |
| ggcagggtcg gaacaggaga gcgcacgagg gagcttccag ggggaaacgc | 5806 |
| ctggtatctt tatagtcctg tcgggtttcg ccacctctga cttgagcgtc | 5856 |
| gatttttgtg atgctcgtca ggggggcgga gcctatggaa aaacgccagc | 5906 |
| aacgcggcct ttttacggtt cctggccttt tgctggcctt ttgctcacat | 5956 |
| gttctttcct gcgttatccc ctgattctgt ggataaccgt attaccgcct | 6006 |
| ttgagtgagc tgataccgct cgccgcagcc gaacgaccga gcgcagcgag | 6056 |
| tcagtgagcg aggaagcgga agagcgccca atacgcaaac cgcctctccc | 6106 |
| cgcgcgttgg ccgattcatt aatgcaggta tcacgaggcc ctttcgtctt | 6156 |
| cac | 6159 |

```
<210> SEQ ID NO 36
<211> LENGTH: 6629
<212> TYPE: DNA
<213> ORGANISM: Artificial Sequence
<220> FEATURE:
<223> OTHER INFORMATION: pREN 19/2 HC DHFR Vector

<400> SEQUENCE: 36
```

| | |
|---|---|
| ctcgagagcg ggcagtgagc gcaacgcaat taatgtgagt tagctcactc | 50 |
| attaggcacc ccaggcttta cactttatgc tcccggctcg tatgttgtgt | 100 |
| ggagattgtg agcggataac aatttcacac agaattcgtg aggctccggt | 150 |
| gcccgtcagt gggcagagcg cacatcgccc acagtccccg agaagttggg | 200 |
| ggagggggtc ggcaattgaa ccggtgccta gagaaggtgg cgcggggtaa | 250 |
| actgggaaag tgatgtcgtg tactggctcc gcctttttcc cgagggtggg | 300 |
| ggagaaccgt ataaagtgc agtagtcgcc gtgaacgttc ttttttcgcaa | 350 |
| cgggtttgcc gccagaacac aggtaagtgc cgtgtgtggt tcccgcgggc | 400 |
| ctggcctctt tacgggttat ggcccttgcg tgccttgaat tacttccacg | 450 |
| cccctggctg cagtacgtga ttcttgatcc cgagcttcgg gttggaagtg | 500 |
| ggtgggagag ttcgaggcct tgcgcttaag gagccccttc gcctcgtgct | 550 |
| tgagttgagg cctggcctgg gcgctgggcc gccgcgtgc gaatctggtg | 600 |
| gcaccttcgc gcctgtctcg ctgctttcga taagtctcta gccatttaaa | 650 |
| attttttgatg acctgctgcg acgctttttt tctggcaaga tagtcttgta | 700 |
| aatgcgggcc aagatctgca cactggtatt tcggtttttg gggccgcggg | 750 |

```
cggcgacggg gcccgtgcgt cccagcgcac atgttcggcg aggcggggcc         800
tgcgagcgcg gccaccgaga atcggacggg ggtagtctca agctggccgg         850
cctgctctgg tgcctggcct cgcgccgccg tgtatcgccc cgccctgggc         900
ggcaaggctg gcccggtcgg caccagttgc gtgagcggaa agatggccgc         950
ttcccggccc tgctgcaggg agctcaaaat ggaggacgcg cgcgctcggga        1000 gagcgggcgg gtgagtcacc cacacaaagg aaaagggcct ttccgtcctc        1050
agccgtcgct tcatgtgact ccacggagta ccgggcgccg tccaggcacc        1100
tcgattagtt ctcgagcttt tggagtacgt cgtctttagg ttgggggggag       1150 gggttttatg cgatggagtt tccccacact gagtgggtgg agactgaagt        1200
taggccagct tggcacttga tgtaattctc cttggaattt gcccttttg         1250 agtttggatc ttggttcatt ctcaagcctc agacagtggt tcaaagtttt       1300
tttcttccat ttcaggtgta cgcgtctcgg gaagctttag tttaaacgcc        1350
```

| | |
|---|---|
| gccacc atg gag ctg atc atg ctc ttc ctc ctg tca gga act<br>       Met Glu Leu Ile Met Leu Phe Leu Leu Ser Gly Thr<br>                      5                        10 | 1392 |
| gca ggc gtc cac tct gag gtc cag ctt cag cag tca gga cct<br>Ala Gly Val His Ser Glu Val Gln Leu Gln Gln Ser Gly Pro<br> 15                   20                   25 | 1434 |
| gaa ctg gtg aaa cct ggg gcc tca gtg aag ata tcc tgc aag<br>Glu Leu Val Lys Pro Gly Ala Ser Val Lys Ile Ser Cys Lys<br>          30                   35                  40 | 1476 |
| gct tct gga tac act ttc act gac tac aac ata cac tgg gtg<br>Ala Ser Gly Tyr Thr Phe Thr Asp Tyr Asn Ile His Trp Val<br>                45                   50 | 1518 |
| aaa cag agc cat gga aag agc ctt gac tgg att gga tat att<br>Lys Gln Ser His Gly Lys Ser Leu Asp Trp Ile Gly Tyr Ile<br>55                 60                    65 | 1560 |
| gct cct tac agt ggt ggt act ggt tac aac cag gag ttc aag<br>Ala Pro Tyr Ser Gly Gly Thr Gly Tyr Asn Gln Glu Phe Lys<br> 70                   75                   80 | 1602 |
| aac agg gcc aca ttg act gta gac aaa tcc tcc agc aca gcc<br>Asn Arg Ala Thr Leu Thr Val Asp Lys Ser Ser Ser Thr Ala<br>          85                   90                  95 | 1644 |
| tac atg gag ctc cgc agt ctg aca tct gat gac tct gca gtc<br>Tyr Met Glu Leu Arg Ser Leu Thr Ser Asp Asp Ser Ala Val<br>                100               105              110 | 1686 |
| tat tac tgt gct aga cga gac cgt ttc cct tat tac ttt gac<br>Tyr Tyr Cys Ala Arg Arg Asp Arg Phe Pro Tyr Tyr Phe Asp<br>          115                   120 | 1728 |
| tac tgg ggc caa ggc acc act ctc aga gtc tcc tca gtgagt<br>Tyr Trp Gly Gln Gly Thr Thr Leu Arg Val Ser Ser<br>125                130                  135 | 1770 |

```
ggatcctctg cgcctgggcc cagctctgtc ccacaccgcg gtcacatggc         1820
```

| | |
|---|---|
| accacctctc ttgcagcc tcc acc aag ggc cca tcg gtc ttc<br>                     Ser Thr Lys Gly Pro Ser Val Phe<br>                                                140 | 1862 |
| ccc ctg gca ccc tcc tcc aag agc acc tct ggg ggc aca<br>Pro Leu Ala Pro Ser Ser Lys Ser Thr Ser Gly Gly Thr<br>145                150                  155 | 1901 |
| gcg gcc ctg ggc tgc ctg gtc aag gac tac ttc ccc gaa ccg<br>Ala Ala Leu Gly Cys Leu Val Lys Asp Tyr Phe Pro Glu Pro<br>          160                   165              170 | 1943 |

| | |
|---|---|
| gtg acg gtg tcg tgg aac tca ggc gcc ctg acc agc ggc gtg<br>Val Thr Val Ser Trp Asn Ser Gly Ala Lys Thr Ser Gly Val<br>            175              180              185 | 1985 |
| cac acc ttc ccg gct gtc cta cag tcc tca gga ctc tac tcc<br>His Thr Phe Pro Ala Val Leu Gln Ser Ser Gly Leu Tyr Ser<br>            190              195 | 2027 |
| ctc agc agc gtg gtg acc gtg ccc tcc agc agc ttg ggc acc<br>Leu Ser Ser Val Val Thr Val Pro Ser Ser Ser Leu Gly Thr<br>200              205              210 | 2069 |
| cag acc tac atc tgc aac gtg aat cac aag ccc agc aac acc<br>Gln Thr Tyr Ile Cys Asn Val Asn His Lys Pro Ser Asn Thr<br>            215              220              225 | 2111 |
| aag gtg gac aag aaa gtt gag ccc aaa tct tgt gac aaa act<br>Lys Val Asp Lys Lys Val Glu Pro Lys Ser Cys Asp Lys Thr<br>            230              235              240 | 2153 |
| cac aca tgc cca ccg tgc cca gca cct gaa ctc ctg ggg gga<br>His Thr Cys Pro Pro Cys Pro Ala Pro Glu Leu Leu Gly Gly<br>            245              250              255 | 2195 |
| ccg tca gtc ttc ctc ttc ccc cca aaa ccc aag gac acc ctc<br>Pro Ser Val Phe Leu Phe Pro Pro Lys Pro Lys Asp Thr Leu<br>                260              265 | 2237 |
| atg atc tcc cgg acc cct gag gtc aca tgc gtg gtg gtg gac<br>Met Ile Ser Arg Thr Pro Glu Val Thr Cys Val Val Val Asp<br>270              275              280 | 2279 |
| gtg agc cac gaa gac cct gag gtc aag ttc aac tgg tac gtg<br>Val Ser His Glu Asp Pro Glu Val Lys Phe Asn Trp Tyr Val<br>            285              290              295 | 2321 |
| gac ggc gtg gag gtg cat aac gcc aag aca aag ccg cgg gag<br>Asp Gly Val Glu Val His Asn Ala Lys Thr Lys Pro Arg Glu<br>                300              305              310 | 2363 |
| gag cag tac aac agc acg tac cgg gtg gtc agc gtc ctc acc<br>Glu Gln Tyr Asn Ser Thr Tyr Arg Val Val Ser Val Leu Thr<br>            315              320              325 | 2405 |
| gtc ctg cac cag gac tgg ctg aat ggc aag gag tac aag tgc<br>Val Leu His Gln Asp Trp Leu Asn Gly Lys Glu Tyr Lys Cys<br>                330              335 | 2447 |
| aag gtc tcc aac aaa gcc ctc cca gcc ccc atc gag aaa acc<br>Lys Val Ser Asn Lys Ala Leu Pro Ala Pro Ile Glu Lys Thr<br>340              345              350 | 2489 |
| atc tcc aaa gcc aaa ggg cag ccc cga gaa cca cag gtg tac<br>Ile Ser Lys Ala Lys Gly Gln Pro Arg Glu Pro Gln Val Tyr<br>            355              360              365 | 2531 |
| acc ctg ccc cca tcc cgg gag gag atg acc aag aac cag gtc<br>Thr Leu Pro Pro Ser Arg Glu Glu Met Thr Lys Asn Gln Val<br>            370              375              380 | 2573 |
| agc ctg acc tgc ctg gtc aaa ggc ttc tat ccc agc gac atc<br>Ser Leu Thr Cys Leu Val Lys Gly Phe Tyr Pro Ser Asp Ile<br>                385              390              395 | 2615 |
| gcc gtg gag tgg gag agc aat ggg cag ccg gag aac aac tac<br>Ala Val Glu Trp Glu Ser Asn Gly Gln Pro Glu Asn Asn Tyr<br>                400              405 | 2657 |
| aag acc acg cct ccc gtg ctg gac tcc gac ggc tcc ttc ttc<br>Lys Thr Thr Pro Pro Val Leu Asp Ser Asp Gly Ser Phe Phe<br>410              415              420 | 2699 |
| ctc tac agc aag ctc acc gtg gac aag agc agg tgg cag cag<br>Leu Tyr Ser Lys Leu Thr Val Asp Lys Ser Arg Trp Gln Gln<br>            425              430              435 | 2741 |
| ggg aac gtc ttc tca tgc tcc gtg atg cat gag gct ctg cac<br>Gly Asn Val Phe Ser Cys Ser Val Met His Glu Ala Leu His<br>            440              445              450 | 2783 |

```
aac cac tac acg cag aag agc ctc tcc ctg tct ccg ggt aaa      2825
Asn His Tyr Thr Gln Lys Ser Leu Ser Leu Ser Pro Gly Lys
             455                 460                 465 tga gctagaaact aactaagcta gcaacggttt ccctctagcg ggatcaattc    2878 cgccccccc ccctaacgtt actggccgaa gccgcttgga ataaggccgg         2928
tgtgcgtttg tctatatgtt attttccacc atattgccgt cttttggcaa        2978
tgtgagggcc cggaaacctg gccctgtctt cttgacgagc attcctaggg        3028
gtctttcccc tctcgccaaa ggaatgcaag gtctgttgaa tgtcgtgaag        3078
gaagcagttc ctctggaagc ttcttgaaga caaacaacgt ctgtagcgac        3128
cctttgcagg cagcggaacc ccccacctgg cgacaggtgc ctctgcggcc        3178
aaaagccacg tgtataagat acacctgcaa aggcggcaca accccagtgc        3228
cacgttgtga gttggatagt tgtggaaaga gtcaaatggc tctcctcaag        3278
cgtattcaac aagggctga aggatgccca gaaggtaccc cattgtatgg         3328
gatctgatct ggggcctcgg tgcacatgct ttacgtgtgt ttagtcgagg        3378
ttaaaaaacg tctaggcccc ccgaaccacg gggacgtggt tttcctttga        3428
aaaacacgat aataccatgg ttcgaccatt gaactgcatc gtcgccgtgt        3478
cccaaaatat ggggattggc aagaacggag acctaccctg gcctccgctc       3528
aggaacgagt tcaagtactt ccaaagaatg accacaacct cttcagtgga        3578
aggtaaacag aatctggtga ttatgggtag gaaaacctgg ttctccattc       3628
ctgagaagaa tcgacccttta aaggacagaa ttaatggttc gatatagttc       3678
tcagtagaga actcaaagaa ccaccacgag gagctcattt tcttgccaaa        3728
agtttggatg atgccttaag acttattgaa caaccggaat tggcaagtaa       3778
agtagacatg gtttggatag tcggaggcag ttctgtttac caggaagcca        3828
tgaatcaacc aggccacctc agactctttg tgacaaggat catgcaggaa        3878
tttgaaagtg acacgttttt cccagaaatt gatttgggga aatataaact        3928
tctcccagaa tacccaggcg tcctctctga ggtccaggag gaaaaaggca        3978
tcaagtataa gtttgaagtc tacgagaaga aagactaaca ggaagatgct        4028
ttcaagttct ctgctcccct cctaaagcta tgcatttta taagaccatg         4078 ggacttttgc tggtcgatcg acctggcgta atagcgaaga ggcccgcacc        4128
gatcgccctt cccaacagtt gcgcagcctg aatggcgaat gggacgcgcc       4178
ctgtagcggc gcattaagcg cggcgggtgt ggtggttacg cgcagcgtga        4228
ccgctacact tgccagcgcc ctagcgcccg ctcctttcgc tttcttccct        4278
tcctttctcg ccacgttcgc cggctttccc cgtcaagctc taaatcgggg        4328
gctcccttta gggttccgat ttagtgcttt acggcacctc gaccccaaaa        4378
aacttgatta gggtgatggt tcacgtagtg gccatcgcc ctgatagacg         4428 gtttttcgcc tttgacgttg gagtccacgt tctttaatag tggactcttg        4478
ttccaaactg gaacaacact caaccctatc tcggtctatt tataagggat        4528
tttgccgatt tcggcctatt ggttaaaaaa tgagctgatt taacaaaatt       4578
taacgcgaat tttaacaaaa tattaacgct tacaatttag gtggcacttt        4628
tcggggaaat gtgcgcggaa ccctatatt tgtttatttt tctaaataca         4678
```

| | |
|---|---|
| ttcaaatatg tatccgctca tgagacaata accctgataa atgcttcaat | 4728 |
| aatattgaaa aaggaagagt atgagtattc aacatttccg tgtcgccctt | 4778 |
| attccctttt ttgcggcatt ttgccttact gttttttgctc acccagaaac | 4828 |
| gctggtgaaa gtaaaagatg ctgaagatca gttgggtgca cgagtgggtt | 4878 |
| acatcgaact ggatctcaac agcggtaaga tccttgagag ttttcgcccc | 4928 |
| gaagaacgtt ttccaatgat gagcactttt aaagttctgc tatgtggcgc | 4978 |
| ggtattatcc cgtattgacg ccgggcaaga gcaactcggt cgccgcatac | 5028 |
| actattctca gaatgacttg gttgagtact caccagtcac agaaaagcat | 5078 |
| attacggatg gcatgacagt aagagaatta tgcagtgctg ccataaccat | 5128 |
| gagtgataac actgcggcca acttacttct gacaacgatc ggaggaccga | 5178 |
| aggagctaac cgcttttttg cacaacatgg gggatcatgt aactcgcctt | 5228 |
| gatcgttggg aaccggagct gaatgaagcc ataccaaacg acgagcgtga | 5278 |
| caccacgatg cctgtagcaa tggcaacaac gttgcgcaaa ctattaactg | 5328 |
| gcgaactact tactctagct tcccggcaac aattaataga ctggatggag | 5378 |
| gcggataaag ttgcaggacc acttctgcgc tcggcccttc cggctggctg | 5428 |
| gtttattgct gataaatctg gagccggtga gcgtgggtct cgcggtatca | 5478 |
| ttgcagcact ggggccagat ggtaagccct cccgtatcgt agttatctac | 5528 |
| acgacgggga gtcaggcaac tatggatgaa cgaaatagac agatcgctga | 5578 |
| gataggtgcc tcactgatta agcattggta actgtcagac caagtttact | 5628 |
| catatatact ttagattgat ttaaaacttc attttttaatt taaaaggatc | 5678 |
| taggtgaaga tcctttttga taatctcatg accaaaatcc cttaacgtga | 5728 |
| gttttcgttc cactgagcgt cagacccccgt agaaaagatc aaaggatgtt | 5778 |
| cttgagatcc ttttttttctg cacgtaatct gctgcttgca acaaaaaaac | 5828 |
| caccgctacc agcggtggtt tgtttgccgg atcaagagct accaactctt | 5878 |
| tttccgaagg taactggctt cagcagagcg cagataccaa atactgtcct | 5928 |
| tctagtgtag ccgtagttag gccaccactt caagaactct gtagcaccgc | 5978 |
| ctacatacct cgctctgcta atcctgttac cagtggctgc tgccagtggc | 6028 |
| gataagtcgt gtcttaccgg gttggactca agacgatagt taccggataa | 6078 |
| ggcgcagcgg tcgggctgaa cggggggttc gtgcacacag cccagcttgg | 6128 |
| agcgaacgac ctacaccgaa ctgagatacc tacagcgtga gctatgagaa | 6178 |
| agcgccacgc ttcccgaagg gagaaaggcg gacaggtatc cggtaagcgg | 6228 |
| cagggtcgga acaggagagc gcacgaggga gcttccaggg ggaaacgcct | 6278 |
| ggtatcttta tagtcctgtc gggtttcgcc acctctgact tgagcgtcga | 6328 |
| tttttgtgat gctcgtcagg gggcggagc ctatggaaaa acgccagcaa | 6378 |
| cgcggccttt ttacggttcc tggccttttg ctggccttt gctcacatgt | 6428 |
| tctttcctgc gttatcccct gattctgtgg ataaccgtat taccgccttt | 6478 |
| gagtgagctg ataccgctcg ccgcagccga acgaccgagc gcagcgagtc | 6528 |
| agtgagcgag gaagcggaag agcgcccaat acgcaaaccg cctctccccg | 6578 |
| cgcgttggcc gattcattaa tgcaggtatc acgaggccct tcgtcttca c | 6629 |

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
ttcttgaagt ctggtgatgc tgcc                                          24

<210> SEQ ID NO 38
<211> LENGTH: 31
<212> TYPE: DNA
<213> ORGANISM: Artificial Sequence
<220> FEATURE:
<223> OTHER INFORMATION: primer

<400> SEQUENCE: 38
caagctagcc ctctaagact cctcccctgt t                                  31

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39
gaactcgagt catttacccg gagacaggga gag                                33

<210> SEQ ID NO 40
<211> LENGTH: 32
<212> TYPE: DNA
<213> ORGANISM: Artificial Sequence
<220> FEATURE:
<223> OTHER INFORMATION: primer

<400> SEQUENCE: 40
gcgccatggc ccaggtgcaa ctgcagcagt ca                                 32

<210> SEQ ID NO 41
<211> LENGTH: 34
<212> TYPE: DNA
<213> ORGANISM: Artificial Sequence
<220> FEATURE:
<223> OTHER INFORMATION: primer

<400> SEQUENCE: 41
cagggatcca ctcacctgag gagacggtga ccgt                               34

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
agcgccatgg acatcgagct cactcagtct cca                                33

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43 caggatcca actcacgttt gatttccagc ttggt                               35

<210> SEQ ID NO 44
<211> LENGTH: 465
<212> TYPE: DNA
<213> ORGANISM: Mus Musculus
<220> FEATURE:
<223> OTHER INFORMATION: nucleotide sequence of murine heavy chain
      variable region

<400> SEQUENCE: 44
gtttaaacgc cgccaccatg aactggacct ggaccgtgtt ttgcctgctc              50
gctgtggctc ctggggccca cagcgccatg gcccaggtgc aactgcagca              100
gtcaggggct gagctggcta gacctggggc ttcagtgaag atgtcctgca              150
aggcttctgg ctacaccttt actacctaca aatacactg ggtaagacag               200 aggcctggac acgatctgga atggattgga tacattaatc ctagcagtgg              250
atattctgac tacaatcaaa gcttcaaggg caagaccaca ttgactgcag              300
acaagtcctc caacacagcc tacatgcaac tgaacagcct gacatctgag              350
gactctgcgg tctattactg tgcaagaaga gcggactatg gtaactacga              400
atatacctgg tttgcttact ggggccaagg gaccacggtc accgtctcct              450
caggtgagtg gatcc                                                    465

<210> SEQ ID NO 45
<211> LENGTH: 145
<212> TYPE: PRT
<213> ORGANISM: Mus musculus
<220> FEATURE:
<223> OTHER INFORMATION: amino acid sequence for murine heavy chain
      variable region

<400> SEQUENCE: 45

Met Asn Trp Thr Trp Thr Val Phe Cys Leu Leu Ala Val Ala Pro Gly
                 5                  10                  15

Ala His Ser Ala Met Ala Gln Val Gln Leu Gln Gln Ser Gly Ala Glu
             20                  25                  30

Leu Ala Arg Pro Gly Ala Ser Val Lys Met Ser Cys Lys Ala Ser Gly
         35                  40                  45

Tyr Thr Phe Thr Thr Tyr Thr Ile His Trp Val Arg Gln Arg Pro Gly
     50                  55                  60

His Asp Leu Glu Trp Ile Gly Tyr Ile Asn Pro Ser Ser Gly Tyr Ser
 65                  70                  75                  80

Asp Tyr Asn Gln Ser Phe Lys Gly Lys Thr Thr Leu Thr Ala Asp Lys
                 85                  90                  95

Ser Ser Asn Thr Ala Tyr Met Gln Leu Asn Ser Leu Thr Ser Glu Asp
            100                 105                 110

Ser Ala Val Tyr Tyr Cys Ala Arg Arg Ala Asp Tyr Gly Asn Tyr Glu
        115                 120                 125

Tyr Thr Trp Phe Ala Tyr Trp Gly Gln Gly Thr Thr Val Thr Val Ser
    130                 135                 140

Ser
145

<210> SEQ ID NO 46
<211> LENGTH: 415

```
<212> TYPE: DNA
<213> ORGANISM: Mus musculus
<220> FEATURE:
<223> OTHER INFORMATION: nucleotide sequence for murine light chain
      variable region

<400> SEQUENCE: 46
gtttaaacgc cgccaccatg aactggacct ggaccgtgtt ttgcctgctc          50
gctgtggctc ctggggccca cagcgccatg acatcgagc tcactcagtc          100 tccaaaattc atgtccacat cagtaggaga cagggtcaac gtcacctaca         150
aggccagtca gaatgtgggt actaatgtag cctggtttca acaaaaacca         200
gggcaatctc ctaaagttct gatttactcg gcatcttacc gatacagtgg         250
agtccctgat cgcttcacag gcagtggatc tggaacagat ttcactctca         300
ccatcagcaa tgtgcagtct gaagacttgg cagagtattt ctgtcagcaa         350
tatcacacct atcctctcac gttcggaggg ggcaccaagc tggaaatcaa         400
acgtgagttg gatcc                                               415

<210> SEQ ID NO 47
<211> LENGTH: 129
<212> TYPE: PRT
<213> ORGANISM: Mus musculus
<220> FEATURE:
<223> OTHER INFORMATION: amino acid sequence for murine light chain
      variable region

<400> SEQUENCE: 47

Met Asn Trp Thr Trp Thr Val Phe Cys Leu Leu Ala Val Ala Pro Gly
                 5                  10                  15

Ala His Ser Ala Met Asp Ile Glu Leu Thr Gln Ser Pro Lys Phe Met
             20                  25                  30

Ser Thr Ser Val Gly Asp Arg Val Asn Val Thr Tyr Lys Ala Ser Gln
         35                  40                  45

Asn Val Gly Thr Asn Val Ala Trp Phe Gln Gln Lys Pro Gly Gln Ser
     50                  55                  60

Pro Lys Val Leu Ile Tyr Ser Ala Ser Tyr Arg Tyr Ser Gly Val Pro
 65                  70                  75                  80

Asp Arg Phe Thr Gly Ser Gly Ser Gly Thr Asp Phe Thr Leu Thr Ile
                 85                  90                  95

Ser Asn Val Gln Ser Glu Asp Leu Ala Glu Tyr Phe Cys Gln Gln Tyr
            100                 105                 110

His Thr Tyr Pro Leu Thr Phe Gly Gly Gly Thr Lys Leu Glu Ile Lys
        115                 120                 125

Arg

<210> SEQ ID NO 48
<211> LENGTH: 5759
<212> TYPE: DNA
<213> ORGANISM: Artificial Sequence
<220> FEATURE:
<223> OTHER INFORMATION: Light chain expression vector pREN-Neo which is
      a mammalian cell expression vector used to produce chimeric and
      reshaped human antibodies with human kappa light chains and human
      gamma-1 heavy chains

<400> SEQUENCE: 48
ctcgagagcg ggcagtgagc gcaacgcaat taatgtgagt tagctcactc          50
attaggcacc ccaggcttta cactttatgc tcccggctcg tatgttgtgt         100
```

-continued

```
ggagattgtg agcggataac aatttcacac agaattcgtg aggctccggt        150
gcccgtcagt gggcagagcg cacatcgccc acagtccccg agaagttggg        200
gggaggggtc ggcaattgaa ccggtgccta gagaaggtgg cgcggggtaa        250
actgggaaag tgatgtcgtg tactggctcc gccttttttcc cgagggtggg       300
ggagaaccgt atataagtgc agtagtcgcc gtgaacgttc tttttcgcaa        350
cgggtttgcc gccagaacac aggtaagtgc cgtgtgtggt cccgcgggc         400
ctggcctctt tacgggttat ggcccttgcg tgccttgaat tacttccacg        450
cccctggctg cagtacgtga ttcttgatcc cgagcttcgg gttggaagtg        500
ggtgggagag ttcgaggcct tgcgcttaag gagccccttc gcctcgtgct        550
tgagttgagg cctggcctgg gcgctggggc cgccgcgtgc gaatctggtg        600
gcaccttcgc gcctgtctcg ctgctttcga taagtctcta gccatttaaa       650
atttttgatg acctgctgcg acgcttttttt tctggcaaga tagtcttgta      700
aatgcgggcc aagatctgca cactggtatt tcggttttttg gggccgcggg      750
cggcgacggg gcccgtgcgt cccagcgcac atgttcggcg aggcggggcc        800
tgcgagcgcg gccaccgaga tcggacgggg gtagtctca agctggccgg         850
cctgctctgg tgcctggcct cgcgccgccg tgtatcgccc cgccctgggc        900
ggcaaggctg gccggtcgg caccagttgc gtgagcggaa agatggccgc         950
ttcccggccc tgctgcaggg agctcaaaat ggaggacgcg gcgctcggga        1000
gagcgggcgg gtgagtcacc cacacaaagg aaaagggcct ttccgtcctc       1050
agccgtcgct tcatgtgact ccacggagta ccgggcgccg tccaggcacc       1100
tcgattagtt ctcgagcttt tggagtacgt cgtctttagg ttgggggag         1150
gggttttatg cgatggagtt tccccacact gagtgggtgg agactgaagt       1200
taggccagct tggcacttga tgtaattctc cttggaattt gccctttttg       1250
agtttggatc ttggttcatt ctcaagcctc agacagtggt tcaaagtttt      1300
tttcttccat ttcaggtgta cgcgtctcgg gaagctttag tttaaacgcc       1350
gtgagtggat ccatctggga taagcatgct gttttctgtc tgtccctaac       1400
atgcccgtgt attatgcgca acaacacac ccaagggcag aactttgtta        1450
cttaaacacc atcctgtttg cttctttcct cagga act gtg gct gca cca    1500
                                       Thr Val Ala Ala Pro
                                                      5
tct gtc ttc atc ttc ccg cca tct gat gag cag ttg aaa tct gga  1545
Ser Val Phe Ile Phe Pro Pro Ser Asp Glu Gln Leu Lys Ser Gly
         10                  15                  20
act gcc tct gtt gtg tgc ctg ctg aat aac ttc tat ccc aga gag  1590
Thr Ala Ser Val Val Cys Leu Leu Asn Asn Phe Tyr Pro Arg Glu
             25                  30                  35
gcc aaa gta cag tgg aag gtg gat aac gcc ctc caa tcg ggt aac  1635
Ala Lys Val Gln Trp Lys Val Asp Asn Ala Leu Gln Ser Gly Asn
         40                  45                  50
tcc cag gag agt gtc aca gag cag gac agc aag gac agc acc tac  1680
Ser Gln Glu Ser Val Thr Glu Gln Asp Ser Lys Asp Ser Thr Tyr
             55                  60                  65
agc ctc agc agc acc ctg acg ctg agc aaa gca gac tac gag aaa  1725
Ser Leu Ser Ser Thr Leu Thr Leu Ser Lys Ala Asp Tyr Glu Lys
         70                  75                  80
```

| | |
|---|---|
| cac aaa gtc tac gcc tgc gaa gtc acc cat cag ggc ctg agc tcg<br>His Lys Val Tyr Ala Cys Glu Val Thr His Gln Gly Leu Ser Ser<br>85 90 95 | 1770 |
| ccc gtc aca aag agc ttc aac agg gga gag tgt tga<br>Pro Val Thr Lys Ser Phe Asn Arg Gly Glu Cys<br>100 105 | 1806 |
| gctagaacta actaactaag ctagcaacgg tttccctcta gcgggatcaa | 1856 |
| ttccgccccc ccccctaac gttactggcc gaagccgctt ggaataaggc | 1906 |
| cggtgtgcgt ttgtctatat gttatttcc accatattgc cgtcttttgg | 1956 |
| caatgtgagg gcccggaaac ctggccctgt cttcttgacg agcattccta | 2006 |
| ggggtctttc ccctctcgcc aaaggaatgc aaggtctgtt gaatgtcgtg | 2056 |
| aaggaagcag ttcctctgga agcttcttga agacaaacaa cgtctgtagc | 2106 |
| gacccttgc aggcagcgga accccccacc tggcgacagg tgcctctgcg | 2156 |
| gccaaaagcc acgtgtataa gatacacctg caaaggcggc acaacccag | 2206 |
| tgccacgttg tgagttggat agttgtggaa agagtcaaat ggctctcctc | 2256 |
| aagcgtattc aacaaggggc tgaaggatgc ccagaaggta ccccattgta | 2306 |
| tgggatctga tctggggcct cggtgcacat gctttacgtg tgtttagtcg | 2356 |
| aggttaaaaa acgtctaggc cccccgaacc acggggacgg ggttttcctt | 2406 |
| tgaaaaacac gataatacca tggttgaaca agatggattg cacgcaggtt | 2456 |
| ctccggccgc ttgggtggag aggctattcg gctatgactg gcacaacag | 2506 |
| acaatcggct gctctgatgc cgccgtgttc cggctgtcag cgcaggggcg | 2556 |
| cccggttctt tttgtcaaga ccgacctgtc cggtgccctg aatgaactgc | 2606 |
| aggacgaggc agcgcggcta tcgtggctgg ccacgacggg cgttccttgc | 2656 |
| gcagctgtgc tcgacgttgt cactgaagcg ggaagggact ggctgctatt | 2706 |
| gggcgaagtg ccggggcagg atctcctgtc atctcacctt gctcctgccg | 2756 |
| agaaagtatc catcatggct gatgcaatgc ggcggctgca tacgcttgat | 2806 |
| ccggctacct gcccattcga ccaccaagcg aaacatcgca tcgagcgagc | 2856 |
| acgtactcgg atggaagccg gtcttgtcga tcaggatgat ctggacgaag | 2906 |
| agcatcaggg gctcgcgcca gccgaactgt tcgccaggct caaggcgcgc | 2956 |
| atgcccgacg gcgaggatct cgtcgtgacc catggcgatg cctgcttgcc | 3006 |
| gaatatcatg gtggaaaatg gccgcttttc tggattcatc gactgtggcc | 3056 |
| ggctgggtgt ggcggaccgc tatcaggaca tagcgttggc tacccgtgat | 3106 |
| attgctgaag agcttggcgg cgaatgggct gaccgcttcc tcgtgcttta | 3156 |
| cggtatcgcc gctcccgatt cgcagcgcat cgccttctat cgccttcttg | 3206 |
| acgagttctt ctgagtcgat cgacctggcg taatagcgaa gaggcccgca | 3256 |
| ccgatcgccc ttcccaacag ttgcgcagcc tgaatggcga atgggacgcg | 3306 |
| ccctgtagcg gcgcattaag cgcggcgggt gtggtggtta cgcgcagcgt | 3356 |
| gaccgctaca cttgccagcg ccctagcgcc cgctcctttc gctttcttcc | 3406 |
| cttcctttct cgccacgttc gccggctttc ccgtcaagc tctaaatcgg | 3456 |
| gggctccctt tagggttccg atttagtgct ttacggcacc tcgaccccaa | 3506 |
| aaaacttgat tagggtgatg gttcacgtag tgggccatcg ccctgataga | 3556 |
| cggtttttcg ccctttgacgt tggagtccac gttctttaat agtggactct | 3606 |

```
tgttccaaac tggaacaaca ctcaaccccta tctcggtcta tttataaggg    3656
attttgccga tttcggccta ttggttaaaa aatgagctga tttaacaaaa    3706
tttaacgcga atttttaacaa aatattaacg cttacaattt aggtggcact    3756
tttcggggaa atgtgcgcgg aaccccctata tttgtttatt tttctaaata   3806
cattcaaata tgtatccgct catgagacaa taaccctgat aaatgcttca    3856
ataatattga aaaggaaga gtatgagtat tcaacatttc cgtgtcgccc     3906
ttattccctt ttttgcggca ttttgcctta ctgttttttgc tcacccagaa   3956
acgctggtga agtaaaaga tgctgaagat cagttgggtg cacgagtggg     4006
ttacatcgaa ctggatctca acagcggtaa gatccttgag agttttcgcc    4056
ccgaagaacg ttttccaatg atgagcactt ttaaagttct gctatgtggc    4106
gcggtattat cccgtattga cgccgggcaa gagcaactcg gtcgccgcat    4156
acactattct cagaatgact tggttgagta ctcaccagtc acagaaaagc    4206
atattacgga tggcatgaca gtaagagaat tatgcagtgc tgccataacc    4256
atgagtgata acactgcggc caacttactt ctgacaacga tcggaggacc    4306
gaaggagcta accgcttttt tgcacaacat gggggatcat gtaactcgcc    4356
ttgatcgttg ggaaccggag ctgaatgaag ccataccaaa cgacgagcgt    4406
gacaccacga tgcctgtagc aatggcaaca acgttgcgca aactattaac    4456
tggcgaacta cttactctag cttcccggca acaattaata gactggatgg    4506
aggcggataa agttgcagga ccacttctgc gctcggccct tccggctggc    4556
tggtttattg ctgataaatc tggagccggt gagcgtgggt ctcgcggtat    4606
cattgcagca ctggggccag atggtaagcc ctcccgtatc gtagttatct    4656
acacgacggg gagtcaggca actatggatg aacgaaatag acagatcgct    4706
gagataggtg cctcactgat taagcattgg taactgtcag accaagttta    4756
ctcatatata ctttagattg atttaaaact tcatttttaa tttaaaagga    4806
tctaggtgaa gatcctttt gataatctca tgaccaaaat cccttaacgt     4856
gagttttcgt tccactgagc gtcagacccc gtagaaaaga tcaaaggatg    4906
ttcttgagat cctttttttc tgcacgtaat ctgctgcttg caaacaaaaa    4956
accaccgcta ccagcggtgg tttgtttgcc ggatcaagag ctaccaactc    5006
tttttccgaa ggtaactggc ttcagcagag cgcagatacc aaatactgtc    5056
cttctagtgt agccgtagtt aggccaccac ttcaagaact ctgtagcacc    5106
gcctacatac ctcgctctgc taatcctgtt accagtggct gctgccagtg    5156
gcgataagtc gtgtcttacc gggttggact caagacgata gttaccggat    5206
aaggcgcagc ggtcgggctg aacggggggt tcgtgcacac agcccagctt    5256
ggagcgaacg acctacaccg aactgagata cctacagcgt gagctatgag    5306
aaagcgccac gcttcccgaa gggagaaagg cggacaggta tccggtaagc    5356
ggcagggtcg gaacaggaga gcgcacgagg gagcttccag ggggaaacgc    5406
ctggtatctt tatagtcctg tcgggtttcg ccacctctga cttgagcgtc    5456
gatttttgtg atgctcgtca ggggggcgga gcctatggaa aaacgccagc    5506
aacgcggcct ttttacggtt cctggccttt tgctggcctt ttgctcacat    5556
```

<210> SEQ ID NO 49
<211> LENGTH: 6207
<212> TYPE: DNA
<213> ORGANISM: Artificial Sequence
<220> FEATURE:
<223> OTHER INFORMATION: Heavy chain expression vector pREN-DHFR which is a mammalian cell expression vector used to produce chimeric and reshaped human antibodies with human kappa light chains and human gamma-1 heavy chains

<400> SEQUENCE: 49

| | |
|---|---|
| gttctttcct gcgttatccc ctgattctgt ggataaccgt attaccgcct | 5606 |
| ttgagtgagc tgataccgct cgccgcagcc gaacgaccga gcgcagcgag | 5656 |
| tcagtgagcg aggaagcgga agagcgccca atacgcaaac cgcctctccc | 5706 |
| cgcgcgttgg ccgattcatt aatgcaggta tcacgaggcc ctttcgtctt cac | 5759 |

| | |
|---|---|
| ctcgagagcg ggcagtgagc gcaacgcaat taatgtgagt tagctcactc | 50 |
| attaggcacc ccaggcttta cactttatgc tccggctcg tatgttgtgt | 100 |
| ggagattgtg agcggataac aatttcacac agaattcgtg aggctccggt | 150 |
| gcccgtcagt gggcagagcg cacatcgccc acagtccccg agaagttggg | 200 |
| gggaggggtc ggcaattgaa ccggtgccta gagaaggtgg cgcggggtaa | 250 |
| actgggaaag tgatgtcgtg tactggctcc gcctttttcc cgagggtggg | 300 |
| ggagaaccgt atataagtgc agtagtcgcc gtgaacgttc ttttcgcaa | 350 |
| cgggtttgcc gccagaacac aggtaagtgc cgtgtgtggt tcccgcgggc | 400 |
| ctggcctctt tacgggttat ggcccttgcg tgccttgaat tacttccacg | 450 |
| cccctggctg cagtacgtga ttcttgatcc cgagcttcgg gttggaagtg | 500 |
| ggtgggagag ttcgaggcct tgcgcttaag gagccccttc gcctcgtgct | 550 |
| tgagttgagg cctggcctgg gcgctggggc cgccgcgtgc gaatctggtg | 600 |
| gcaccttcgc gcctgtctcg ctgctttcga taagtctcta gccatttaaa | 650 |
| attttgatg acctgctgcg acgctttttt tctggcaaga gtcttgta | 700 |
| aatgcgggcc aagatctgca cactggtatt tcggtttttg gggccgcggg | 750 |
| cggcgacggg gcccgtgcgt cccagcgcac atgttcggcg aggcggggcc | 800 |
| tgcgagcgcg gccaccgaga tcggacgggg gtagtctca agctggccgg | 850 |
| cctgctctgg tgcctggcct cgcgccgccg tgtatcgccc cgccctgggc | 900 |
| ggcaaggctg gcccggtcgg caccagttgc gtgagcggaa agatggccgc | 950 |
| ttcccggccc tgctgcaggg agctcaaaat ggaggacgcg gcgctcggga | 1000 |
| gagcgggcgg gtgagtcacc cacacaaagg aaaagggcct ttccgtcctc | 1050 |
| agccgtcgct tcatgtgact ccacggagta ccgggcgccg tccaggcacc | 1100 |
| tcgattagtt ctcgagcttt tggagtacgt cgtctttagg ttgggggag | 1150 |
| gggttttatg cgatggagtt tccccacact gagtgggtgg agactgaagt | 1200 |
| taggccagct tggcacttga tgtaattctc cttggaattt gccctttttg | 1250 |
| agtttggatc ttggttcatt ctcaagcctc agacagtggt tcaaagtttt | 1300 |
| cttccatttc aggtgtacgc gtctcgggaa gctttagttt aaacgcctgg | 1350 |
| atcctctgcg cctgggccca gctctgtccc acaccgcggt cacatggcac | 1400 |
| cacctctctt gcagcc tcc acc aag ggc cca tcg gtc ttc ccc ctg | 1446 |
|                       Ser Thr Lys Gly Pro Ser Val Phe Pro Leu | |

```
                            -continued
                       5                    10
gca ccc tcc tcc aag agc acc tct ggg ggc aca gcg gcc ctg ggc          1491
Ala Pro Ser Ser Lys Ser Thr Ser Gly Gly Thr Ala Ala Leu Gly
                       15                   20                  25 tgc ctg gtc aag gac tac ttc ccc gaa ccg gtg acg gtg tcg tgg          1536
Cys Leu Val Lys Asp Tyr Phe Pro Glu Pro Val Thr Val Ser Trp
                       30                   35                  40 aac tca ggc gcc ctg acc agc ggc gtg cac acc ttc ccg gct gtc          1581
Asn Ser Gly Ala Leu Thr Ser Gly Val His Thr Phe Pro Ala Val
                       45                   50                  55 cta cag tcc tca gga ctc tac tcc ctc agc agc gtg gtg acc gtg          1626
Leu Gln Ser Ser Gly Leu Tyr Ser Leu Ser Ser Val Val Thr Val
                       60                   65                  70 ccc tcc agc agc ttg ggc acc cag acc tac atc tgc aac gtg aat          1671
Pro Ser Ser Ser Leu Gly Thr Gln Thr Tyr Ile Cys Asn Val Asn
                       75                   80                  85 cac aag ccc agc aac acc aag gtg gac aag aaa gtt gag ccc aaa          1716
His Lys Pro Ser Asn Thr Lys Val Asp Lys Lys Val Glu Pro Lys
                       90                   95                  100 tct tgt gac aaa act cac aca tgc cca ccg tgc cca gca cct gaa          1761
Ser Cys Asp Lys Thr His Thr Cys Pro Pro Cys Pro Ala Pro Glu
                       105                  110                 115 ctc ctg ggg gga ccg tca gtc ttc ctc ttc ccc cca aaa ccc aag          1806
Leu Leu Gly Gly Pro Ser Val Phe Leu Phe Pro Pro Lys Pro Lys
                       120                  125                 130 gac acc ctc atg atc tcc cgg acc cct gag gtc aca tgc gtg gtg          1851
Asp Thr Leu Met Ile Ser Arg Thr Pro Glu Val Thr Cys Val Val
                       135                  140                 145 gtg gac gtg agc cac gaa gac cct gag gtc aag ttc aac tgg tac          1896
Val Asp Val Ser His Glu Asp Pro Glu Val Lys Phe Asn Trp Tyr
                       150                  155                 160 gtg gac ggc gtg gag gtg cat aac gcc aag aca aag ccg cgg gag          1941
Val Asp Gly Val Glu Val His Asn Ala Lys Thr Lys Pro Arg Glu
                       165                  170                 175 gag cag tac aac agc acg tac cgg gtg gtc agc gtc ctc acc gtc          1986
Glu Gln Tyr Asn Ser Thr Tyr Arg Val Val Ser Val Leu Thr Val
                       180                  185                 190 ctg cac cag gac tgg ctg aat ggc aag gag tac aag tgc aag gtc          2031
Leu His Gln Asp Trp Leu Asn Gly Lys Glu Tyr Lys Cys Lys Val
                       195                  200                 205 tcc aac aaa gcc ctc cca gcc ccc atc gag aaa acc atc tcc aaa          2076
Ser Asn Lys Ala Leu Pro Ala Pro Ile Glu Lys Thr Ile Ser Lys
                       210                  215                 220 gcc aaa ggg cag ccc cga gaa cca cag gtg tac acc ctg ccc cca          2121
Ala Lys Gly Gln Pro Arg Glu Pro Gln Val Tyr Thr Leu Pro Pro
                       225                  230                 235 tcc cgg gag gag atg acc aag aac cag gtc agc ctg acc tgc ctg          2166
Ser Arg Glu Glu Met Thr Lys Asn Gln Val Ser Leu Thr Cys Leu
                       240                  245                 250 gtc aaa ggc ttc tat ccc agc gac atc gcc gtg gag tgg gag agc          2211
Val Lys Gly Phe Tyr Pro Ser Asp Ile Ala Val Glu Trp Glu Ser
                       255                  260                 265 aat ggg cag ccg gag aac aac tac aag acc acg cct ccc gtg ctg          2256
Asn Gly Gln Pro Glu Asn Asn Tyr Lys Thr Thr Pro Pro Val Leu
                       270                  275                 280 gac tcc gac ggc tcc ttc ttc ctc tac agc aag ctc acc gtg gac          2301
Asp Ser Asp Gly Ser Phe Phe Leu Tyr Ser Lys Leu Thr Val Asp
                       285                  290                 295 aag agc agg tgg cag cag ggg aac gtc ttc tca tgc tcc gtg atg          2346
```

| | | |
|---|---|---|
| Lys Ser Arg Trp Gln Gln Gly Asn Val Phe Ser Cys Ser Val Met<br>              300                      305                  310 | | |
| cat gag gct ctg cac aac cac tac acg cag aag agc ctc tcc ctg<br>His Glu Ala Leu His Asn His Tyr Thr Gln Lys Ser Leu Ser Leu<br>              315                      320                  325 | | 2391 |
| tct ccg ggt aaa tga gctagaaact aactaagcta gcaacggttt<br>Ser Pro Gly Lys | | 2436 |
| ccctctagcg ggatcaattc cgccccccc cctaacgtt actggccgaa | | 2486 |
| gccgcttgga ataaggccgg tgtgcgtttg tctatatgtt attttccacc | | 2536 |
| atattgccgt cttttggcaa tgtgagggcc cggaaacctg gccctgtctt | | 2586 |
| cttgacgagc attcctaggg gtctttcccc tctcgccaaa ggaatgcaag | | 2636 |
| gtctgttgaa tgtcgtgaag gaagcagttc ctctggaagc ttcttgaaga | | 2686 |
| caaacaacgt ctgtagcgac cctttgcagg cagcggaacc ccccacctgg | | 2736 |
| cgacaggtgc ctctgcggcc aaaagccacg tgtataagat acacctgcaa | | 2786 |
| aggcggcaca accccagtgc cacgttgtga gttggatagt tgtggaaaga | | 2836 |
| gtcaaatggc tctcctcaag cgtattcaac aaggggctga aggatgccca | | 2886 |
| gaaggtaccc cattgtatgg gatctgatct ggggcctcgg tgcacatgct | | 2936 |
| ttacgtgtgt ttagtcgagg ttaaaaaacg tctaggcccc cgaaccacg | | 2986 |
| gggacgtggt tttccttga aaaacacgat aataccatgg ttcgaccatt | | 3036 |
| gaactgcatc gtcgccgtgt cccaaaatat ggggattggc aagaacggag | | 3086 |
| acctaccctg gcctccgctc aggaacgagt tcaagtactt ccaaagaatg | | 3136 |
| accacaacct cttcagtgga aggtaaacag aatctggtga ttatgggtag | | 3186 |
| gaaaacctgg ttctccattc ctgagaagaa tcgacccttta aaggacagaa | | 3236 |
| ttaatggttc gatatagttc tcagtagaga actcaaagaa ccaccacgag | | 3286 |
| gagctcattt tcttgccaaa agtttggatg atgccttaag acttattgaa | | 3336 |
| caaccggaat tggcaagtaa agtagacatg gtttggatag tcggaggcag | | 3386 |
| ttctgtttac caggaagcca tgaatcaacc aggccacctc agactctttg | | 3436 |
| tgacaaggat catgcaggaa tttgaaagtg acacgttttt cccagaaatt | | 3486 |
| gatttgggga aatataaact tctcccagaa tacccaggcg tcctctctga | | 3536 |
| ggtccaggag gaaaaaggca tcaagtataa gtttgaagtc tacgagaaga | | 3586 |
| aagactaaca ggaagatgct ttcaagttct ctgctcccct cctaaagcta | | 3636 |
| tgcattttta taagaccatg ggacttttgc tggtcgatcg acctggcgta | | 3686 |
| atagcgaaga ggcccgcacc gatcgccctt cccaacagtt gcgcagcctg | | 3736 |
| aatggcgaat gggacgcgcc ctgtagcggc gcattaagcg cggcgggtgt | | 3786 |
| ggtggttacg cgcagcgtga ccgctacact gccagcgcc ctagcgcccg | | 3836 |
| ctcctttcgc tttcttccct tcctttctcg ccacgttcgc cggctttccc | | 3886 |
| cgtcaagctc taaatcgggg gctccctta gggttccgat ttagtgcttt | | 3936 |
| acggcacctc gaccccaaaa aacttgatta gggtgatggt tcacgtagtg | | 3986 |
| ggccatcgcc ctgatagacg ttttttcgcc tttgacgttg gagtccacgt | | 4036 |
| tctttaatag tggactcttg ttccaaactg gaacaacact caaccctatc | | 4086 |
| tcggtctatt tataagggat tttgccgatt tcggcctatt ggttaaaaaa | | 4136 |
| tgagctgatt taacaaaatt taacgcgaat tttaacaaaa tattaacgct | | 4186 |

```
tacaatttag gtggcacttt tcggggaaat gtgcgcggaa ccctatatt      4236
tgtttatttt tctaaataca ttcaaatatg tatccgctca tgagacaata     4286
accctgataa atgcttcaat aatattgaaa aaggaagagt atgagtattc     4336
aacatttccg tgtcgccctt attccctttt tgcggcatt ttgccttact      4386
gttttgctc acccagaaac gctggtgaaa gtaaaagatg ctgaagatca      4436
gttgggtgca cgagtgggtt acatcgaact ggatctcaac agcggtaaga    4486
tccttgagag ttttcgcccc gaagaacgtt ttccaatgat gagcactttt    4536
aaagttctgc tatgtggcgc ggtattatcc cgtattgacg ccgggcaaga   4586
gcaactcggt cgccgcatac actattctca gaatgacttg gttgagtact    4636
caccagtcac agaaaagcat attacggatg gcatgacagt aagagaatta   4686
tgcagtgctg ccataaccat gagtgataac actgcggcca acttacttct   4736
gacaacgatc ggaggaccga aggagctaac cgcttttttg cacaacatgg   4786
gggatcatgt aactcgcctt gatcgttggg aaccggagct gaatgaagcc   4836
ataccaaacg acgagcgtga caccacgatg cctgtagcaa tggcaacaac   4886
gttgcgcaaa ctattaactg gcgaactact tactctagct tcccggcaac   4936
aattaataga ctggatggag gcggataaag ttgcaggacc acttctgcgc   4986
tcggcccttc cggctggctg gtttattgct gataaatctg gagccggtga   5036
gcgtgggtct cgcggtatca ttgcagcact ggggccagat ggtaagccct   5086
cccgtatcgt agttatctac acgacgggga gtcaggcaac tatggatgaa   5136
cgaaatagac agatcgctga gataggtgcc tcactgatta agcattggta   5186
actgtcagac caagtttact catatatact ttagattgat ttaaaacttc    5236
atttttaatt taaaaggatc taggtgaaga tccttttga taatctcatg     5286
accaaaatcc cttaacgtga gttttcgttc cactgagcgt cagaccccgt    5336
agaaaagatc aaaggatgtt cttgagatcc tttttttctg cacgtaatct    5386
gctgcttgca acaaaaaac caccgctacc agcggtggtt tgtttgccgg    5436
atcaagagct accaactctt tttccgaagg taactggctt cagcagagcg   5486
cagataccaa atactgtcct tctagtgtag ccgtagttag gccaccactt   5536
caagaactct gtagcaccgc ctacatacct cgctctgcta atcctgttac   5586
cagtggctgc tgccagtggc gataagtcgt gtcttaccgg gttggactca   5636
agacgatagt taccggataa ggcgcagcgg tcgggctgaa cggggggttc   5686
gtgcacacag cccagcttgg agcgaacgac ctacaccgaa ctgagatacc   5736
tacagcgtga gctatgagaa agcgccacgc ttcccgaagg gagaaaggcg   5786
gacaggtatc cggtaagcgg cagggtcgga acaggagagc gcacgaggga   5836
gcttccaggg ggaaacgcct ggtatcttta tagtcctgtc gggtttcgcc   5886
acctctgact tgagcgtcga ttttgtgat gctcgtcagg ggggcggagc    5936
ctatggaaaa acgccagcaa cgcggccttt ttacggttcc tggccttttg   5986
ctggcctttt gctcacatgt tctttcctgc gttatcccct gattctgtgg   6036
ataaccgtat taccgccttt gagtgagctg ataccgctcg ccgcagccga   6086
acgaccgagc gcagcgagtc agtgagcgag gaagcggaag agcgcccaat   6136
```

```
acgcaaaccg cctctccccg cgcgttggcc gattcattaa tgcaggtatc    6186
acgaggccct tcgtcttca c                                    6207
```

<210> SEQ ID NO 50
<211> LENGTH: 444
<212> TYPE: DNA
<213> ORGANISM: Mus musculus
<220> FEATURE:
<223> OTHER INFORMATION: murine G250 heavy chain variable region

<400> SEQUENCE: 50

```
gtttaaacgc cgccaccatg aacttcgggc tcagattgat tttccttgtc    50
ctggttttaa aaggtgtcct gtgtgacgtg aagctcgtgg agtctggggc    100
agccttagtg aagcttggag ggtccctgaa actctcctgt gcagcctctg    150
gattcacttt cagtaactat tacatgtctt gggttcgcca gactccagag    200
aagaggctgg agttggtcgc agccattaat agtgatggtg gtatcaccta    250
ctatctagac actgtgaagg gccgattcac catttcaaga gacaatgcca    300
agaacaccct gtacctgcaa atgagcagtc tgaagtctga ggacacagcc    350
ttgttttact gtgcaagaca ccgctcaggc tacttttcta tggactactg    400
gggtcaagga acctcagtca ccgtctcctc aggtgagtgg atcc         444
```

<210> SEQ ID NO 51
<211> LENGTH: 140
<212> TYPE: PRT
<213> ORGANISM: Mus musculus
<220> FEATURE:
<223> OTHER INFORMATION: amino acid sequence for murine G250 heavy chain
      variable region

<400> SEQUENCE: 51

```
Met Asn Phe Gly Leu Arg Leu Ile Phe Leu Val Leu Val Leu Lys Gly
              5                  10                  15

Val Leu Cys Asp Val Lys Leu Val Glu Ser Gly Ala Ala Leu Val Lys
         20                  25                  30

Leu Gly Gly Ser Leu Lys Leu Ser Cys Ala Ala Ser Gly Phe Thr Phe
     35                  40                  45

Ser Asn Tyr Tyr Met Ser Trp Val Arg Gln Thr Pro Glu Lys Arg Leu
 50                  55                  60

Glu Leu Val Ala Ala Ile Asn Ser Asp Gly Gly Ile Thr Tyr Tyr Leu
65                  70                  75                  80

Asp Thr Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Leu
            100                 105                 110

Phe Tyr Cys Ala Arg His Arg Ser Gly Tyr Phe Ser Met Asp Tyr Trp
        115                 120                 125

Gly Gln Gly Thr Ser Val Thr Val Ser Ser Gly Glu
    130                 135                 140
```

<210> SEQ ID NO 52
<211> LENGTH: 423
<212> TYPE: DNA
<213> ORGANISM: Mus musculus
<220> FEATURE:
<223> OTHER INFORMATION: murine G250 light chain variable region

<400> SEQUENCE: 52

-continued

```
gtttaaacgc cgccaccatg ggcttcaaga tggagtttca tactcaggtc          50
tttgtattcg tgtttctctg gttgtctggt gttgatggag acattgtgat         100
gacccagtct caaagattca tgtccacaac agtaggagac agggtcagca         150
tcacctgcaa ggccagtcag aatgtggttt ctgctgttgc ctggtatcaa         200
cagaaaccag gacaatctcc taaactactg atttactcag catccaatcg         250
gtacactgga gtccctgatc gcttcacagg cagtggatct gggacagatt         300
tcactctcac cattagcaat atgcagtctg aagacctggc tgattttttc         350
tgtcaacaat atagcaacta ccgtggacg ttcggtggag gcaccaagct          400
ggaaatcaaa cgtgagtgga tcc                                       423
```

```
<210> SEQ ID NO 53
<211> LENGTH: 132
<212> TYPE: PRT
<213> ORGANISM: Mus musculus
<220> FEATURE:
<223> OTHER INFORMATION: amino acid sequence for murine G250 light chain
      variable region

<400> SEQUENCE: 53
```

Met Gly Phe Lys Met Glu Phe His Thr Gln Val Phe Val Phe
              5                  10                  15

Leu Trp Leu Ser Gly Val Asp Gly Asp Ile Val Met Thr Gln Ser Gln
           20                  25                  30

Arg Phe Met Ser Thr Thr Val Gly Asp Arg Val Ser Ile Thr Cys Lys
       35                  40                  45

Ala Ser Gln Asn Val Val Ser Ala Val Ala Trp Tyr Gln Gln Lys Pro
   50                  55                  60

Gly Gln Ser Pro Lys Leu Leu Ile Tyr Ser Ala Ser Asn Arg Tyr Thr
65                  70                  75                  80

Gly Val Pro Asp Arg Phe Thr Gly Ser Gly Ser Gly Thr Asp Phe Thr
                   85                  90                  95

Leu Thr Ile Ser Asn Met Gln Ser Glu Asp Leu Ala Asp Phe Phe Cys
              100                 105                 110

Gln Gln Tyr Ser Asn Tyr Pro Trp Thr Phe Gly Gly Gly Thr Lys Leu
          115                 120                 125

Glu Ile Lys Arg
      130

```
<210> SEQ ID NO 54
<211> LENGTH: 482
<212> TYPE: DNA
<213> ORGANISM: Homo sapiens
<220> FEATURE:
<223> OTHER INFORMATION: nucleotide sequence of a TNF fragment

<400> SEQUENCE: 54
```

```
ccatggtctc atcttctcga accccgagtg acaagcctgt agcccatgtt          50
gtagcaaacc ctcaagctga ggggcagctc cagtggctga accgccgggc         100
caatgccctc ctggccaatg gcgtggagct gagagataac cagctggtgg         150
tgccatcaga gggcctgtac ctcatctact cccaggtcct cttcaagggc         200
caaggctgcc cctccaccca tgtgctcctc acccacacca tcagccgcat         250
cgccgtctcc taccagacca aggtcaacct cctctctgcc atcaagagcc         300
```

```
cctgccagag ggagacccca gagggggctg aggccaagcc ctggtatgag        350
cccatctatc tgggaggggt cttccagctg gagaaggtg accgactcag          400 cgctgagatc aatcggcccg actatctcga ctttgccgag tctgggcagg         450
tctactttgg gatcattgcc ctgtgatcta ga                            482

<210> SEQ ID NO 55
<211> LENGTH: 157
<212> TYPE: PRT
<213> ORGANISM: Homo sapiens
<220> FEATURE:
<223> OTHER INFORMATION: amino acid sequence of a TNF fragment

<400> SEQUENCE: 55

Met Val Ser Ser Arg Thr Pro Ser Asp Lys Pro Val Ala His Val
                 5                  10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 56
<211> LENGTH: 6047
<212> TYPE: DNA
<213> ORGANISM: Artificial Sequence
<220> FEATURE:
<223> OTHER INFORMATION: Heavy chain expression vector pREN-DHFR-TNF
      which is a mammalian cell expression vector used to produce
      chimeric and reshaped human antibodies with parts of the human
      gamma-1 heavy chain followed by human TNF after the IgG1 hinge
      region.

<400> SEQUENCE: 56
ctcgagagcg ggcagtgagc gcaacgcaat taatgtgagt tagctcactc         50
attaggcacc ccaggcttta cactttatgc tccggctcg tatgttgtgt          100 ggagattgtg agcggataac aatttcacac agaattcgtg aggctccggt         150
gcccgtcagt gggcagagcg cacatcgccc acagtccccg agaagttggg         200 ggaggggtc ggcaattgaa ccggtgccta gagaaggtgg cgcggggtaa          250
actgggaaag tgatgtcgtg tactggctcc gcctttttcc cgagggtggg         300
ggagaaccgt atataagtgc agtagtcgcc gtgaacgttc tttttcgcaa         350
cgggtttgcc gccagaacac aggtaagtgc cgtgtgtggt tcccgcgggc         400
ctggcctctt tacgggttat ggcccttgcg tgccttgaat tacttccacg         450
```

| | |
|---|---|
| ccctggctg cagtacgtga ttcttgatcc cgagcttcgg gttggaagtg | 500 |
| ggtgggagag ttcgaggcct tgcgcttaag gagccccttc gcctcgtgct | 550 |
| tgagttgagg cctggcctgg gcgctggggc cgccgcgtgc gaatctggtg | 600 |
| gcaccttcgc gcctgtctcg ctgctttcga taagtctcta gccatttaaa | 650 |
| atttttgatg acctgctgcg acgctttttt tctggcaaga tagtcttgta | 700 |
| aatgcgggcc aagatctgca cactggtatt tcggttttg gggccgcggg | 750 |
| cggcgacggg gcccgtgcgt cccagcgcac atgttcggcg aggcgggcc | 800 |
| tgcgagcgcg gccaccgaga tcggacgggg gtagtctca agctggccgg | 850 |
| cctgctctgg tgcctggcct cgcgccgccg tgtatcgccc cgccctgggc | 900 |
| ggcaaggctg gcccggtcgg caccagttgc gtgagcggaa agatggccgc | 950 |
| ttcccggccc tgctgcaggg agctcaaaat ggaggacgcg cgcgctcggga | 1000 |
| gagcgggcgg gtgagtcacc cacacaaagg aaaagggcct ttccgtcctc | 1050 |
| agccgtcgct tcatgtgact ccacggagta ccgggcgccg tccaggcacc | 1100 |
| tcgattagtt ctcgagcttt tggagtacgt cgtctttagg ttgggggag | 1150 |
| gggttttatg cgatggagtt tccccacact gagtgggtgg agactgaagt | 1200 |
| taggccagct tggcacttga tgtaattctc cttggaattt gccctttttg | 1250 |
| agtttggatc ttggttcatt ctcaagcctc agacagtggt tcaaagtttt | 1300 |
| tttcttccat ttcaggtgta cgcgtctcgg gaagctttag tttaaacgcc | 1350 |
| ggatcctctg cgcctgggcc cagctctgtc ccacaccgcg gtcacatggc | 1400 |
| accacctctc ttgcagcc tcc acc aag ggc cca tcg gtc ttc ccc ctg<br>                              Ser Thr Lys Gly Pro Ser Val Phe Pro Leu<br>                                         5                            10 | 1448 |
| gca ccc tcc tcc aag agc acc tct ggg ggc aca gcg gcc ctg ggc<br>Ala Pro Ser Ser Lys Ser Thr Ser Gly Gly Thr Ala Ala Leu Gly<br>              15                       20                   25 | 1493 |
| tgc ctg gtc aag gac tac ttc ccc gaa ccg gtg acg gtg tcg tgg<br>Cys Leu Val Lys Asp Tyr Phe Pro Glu Pro Val Thr Val Ser Trp<br>             30                      35                   40 | 1538 |
| aac tca ggc gcc ctg acc agc ggc gtg cac acc ttc ccg gct gtc<br>Asn Ser Gly Ala Leu Thr Ser Gly Val His Thr Phe Pro Ala Val<br>             45                      50                   55 | 1583 |
| cta cag tcc tca gga ctc tac tcc ctc agc agc gtg gtg acc gtg<br>Leu Gln Ser Ser Gly Leu Tyr Ser Leu Ser Ser Val Val Thr Val<br>             60                      65                   70 | 1628 |
| ccc tcc agc agc ttg ggc acc cag acc tac atc tgc aac gtg aat<br>Pro Ser Ser Ser Leu Gly Thr Gln Thr Tyr Ile Cys Asn Val Asn<br>             75                      80                   85 | 1673 |
| cac aag ccc agc aac acc aag gtg gac aag aaa gtt gag ccc aaa<br>His Lys Pro Ser Asn Thr Lys Val Asp Lys Lys Val Glu Pro Lys<br>             90                      95                  100 | 1718 |
| tct tgt gac aaa act cac aca tgc cca ccg tgc cca ggt gga ggt<br>Ser Cys Asp Lys Thr His Thr Cys Pro Pro Cys Pro Gly Gly Gly<br>             105                   110                 115 | 1763 |
| gga tca cca atg gtc tca tct tct cga acc ccg agt gac aag cct<br>Gly Ser Pro Met Val Ser Ser Ser Arg Thr Pro Ser Asp Lys Pro<br>             120                   125                 130 | 1808 |
| gta gcc cat gtt gta gca aac cct caa gct gag ggg cag ctc cag<br>Val Ala His Val Val Ala Asn Pro Gln Ala Glu Gly Gln Leu Gln<br>             135                   140                 145 | 1853 |

```
tgg ctg aac cgc cgg gcc aat gcc ctc ctg gcc aat ggc gtg gag         1898
Trp Leu Asn Arg Arg Ala Asn Ala Leu Leu Ala Asn Gly Val Glu
            150                 155                 160 ctg aga gat aac cag ctg gtg gtg cca tca gag ggc ctg tac ctc         1943
Leu Arg Asp Asn Gln Leu Val Val Pro Ser Glu Gly Leu Tyr Leu
            165                 170                 175 atc tac tcc cag gtc ctc ttc aag ggc caa ggc tgc ccc tcc acc         1988
Ile Tyr Ser Gln Val Leu Phe Lys Gly Gln Gly Cys Pro Ser Thr
            180                 185                 190 cat gtg ctc ctc acc cac acc atc agc cgc atc gcc gtc tcc tac         2033
His Val Leu Leu Thr His Thr Ile Ser Arg Ile Ala Val Ser Tyr
            195                 200                 205 cag acc aag gtc aac ctc ctc tct gcc atc aag agc ccc tgc cag         2078
Gln Thr Lys Val Asn Leu Leu Ser Ala Ile Lys Ser Pro Cys Gln
            210                 215                 220 agg gag acc cca gag ggg gct gag gcc aag ccc tgg tat gag ccc         2123
Arg Glu Thr Pro Glu Gly Ala Glu Ala Lys Pro Trp Tyr Glu Pro
            225                 230                 235 atc tat ctg gga ggg gtc ttc cag ctg gag aag ggt gac cga ctc         2168
Ile Tyr Leu Gly Gly Val Phe Gln Leu Glu Lys Gly Asp Arg Leu
            240                 245                 250 agc gct gag atc aat cgg ccc gac tat ctc gac ttt gcc gag tct         2213
Ser Ala Glu Ile Asn Arg Pro Asp Tyr Leu Asp Phe Ala Glu Ser
            255                 260                 265 ggg cag gtc tac ttt ggg atc att gcc ctg tga tctagaaact              2256
Gly Gln Val Tyr Phe Gly Ile Ile Ala Leu
            270                 275 aactaagcta gcaacggttt ccctctagcg ggatcaattc cgccccccc              2306 ccctaacgtt actggccgaa gccgcttgga ataaggccgg tgtgcgtttg              2356
tctatatgtt attttccacc atattgccgt cttttggcaa tgtgagggcc              2406
cggaaacctg gccctgtctt cttgacgagc attcctaggg gtctttcccc              2456
tctcgccaaa ggaatgcaag gtctgttgaa tgtcgtgaag gaagcagttc              2506
ctctggaagc ttcttgaaga caaacaacgt ctgtagcgac cctttgcagg              2556
cagcggaacc ccccacctgg cgacaggtgc ctctgcggcc aaaagccacg              2606
tgtataagat acacctgcaa aggcggcaca accccagtgc cacgttgtga              2656
gttggatagt tgtggaaaga gtcaaatggc tctcctcaag cgtattcaac              2706
aaggggctga aggatgccca gaaggtaccc cattgtatgg gatctgatct              2756
ggggcctcgg tgcacatgct ttacgtgtgt ttagtcgagg ttaaaaaacg              2806
tctaggcccc ccgaaccacg gggacgtggt tttcctttga aaaacacgat              2856
aataccatgg ttcgaccatt gaactgcatc gtcgccgtgt cccaaaatat              2906
ggggattggc aagaacggag acctaccctg gcctccgctc aggaacgagt              2956
tcaagtactt ccaagaatg accacaacct cttcagtgga aggtaaacag              3006
aatctggtga ttatgggtag gaaaacctgg ttctccattc ctgagaagaa              3056 tcgacccttta aaggacagaa ttaatggttc gatatagttc tcagtagaga             3106
actcaaagaa ccaccacgag gagctcattt tcttgccaaa agtttggatg              3156
atgccttaag acttattgaa caaccggaat tggcaagtaa agtagacatg              3206
gtttggatag tcggaggcag ttctgtttac caggaagcca tgaatcaacc              3256
aggccacctc agactctttg tgacaaggat catgcaggaa tttgaaagtg              3306
acacgttttt cccagaaatt gatttgggga aatataaact tctcccagaa              3356
```

-continued

```
tacccaggcg tcctctctga ggtccaggag gaaaaaggca tcaagtataa      3406
gtttgaagtc tacgagaaga aagactaaca ggaagatgct ttcaagttct      3456
ctgctcccct cctaaagcta tgcattttta taagaccatg gacttttgc      3506
tggtcgatcg acctggcgta atagcgaaga ggcccgcacc gatcgccctt      3556
cccaacagtt gcgcagcctg aatggcgaat gggacgcgcc ctgtagcggc      3606
gcattaagcg cggcgggtgt ggtggttacg cgcagcgtga ccgctacact      3656
tgccagcgcc ctagcgcccg ctcctttcgc tttcttccct ccttttctcg      3706
ccacgttcgc cggctttccc cgtcaagctc taaatcgggg gctcccttta      3756
gggttccgat ttagtgcttt acggcacctc gaccccaaaa aacttgatta      3806
gggtgatggt tcacgtagtg ggccatcgcc ctgatagacg gttttttcgcc     3856
tttgacgttg gagtccacgt tctttaatag tggactcttg ttccaaactg      3906
gaacaacact caaccctatc tcggtctatt tataagggat tttgccgatt      3956
tcggcctatt ggttaaaaaa tgagctgatt taacaaaatt taacgcgaat      4006
tttaacaaaa tattaacgct tacaatttag gtggcacttt tcggggaaat      4056
gtgcgcggaa cccctatatt tgtttatttt tctaaataca ttcaaatatg      4106
tatccgctca tgagacaata accctgataa atgcttcaat aatattgaaa      4156
aaggaagagt atgagtattc aacatttccg tgtcgccctt attccctttt      4206
tgcggcatt ttgccttact gttttttgctc acccagaaac gctggtgaaa      4256
gtaaaagatg ctgaagatca gttgggtgca cgagtgggtt acatcgaact      4306
ggatctcaac agcggtaaga tccttgagag ttttcgcccc gaagaacgtt      4356
ttccaatgat gagcactttt aaagttctgc tatgtggcgc ggtattatcc      4406
cgtattgacg ccgggcaaga gcaactcggt cgccgcatac actattctca      4456
gaatgacttg gttgagtact caccagtcac agaaaagcat attacggatg      4506
gcatgacagt aagagaatta tgcagtgctg ccataaccat gagtgataac      4556
actgcggcca acttacttct gacaacgatc ggaggaccga aggagctaac      4606
cgcttttttg cacaacatgg gggatcatgt aactcgcctt gatcgttggg      4656
aaccggagct gaatgaagcc ataccaaacg acgagcgtga ccacgatg       4706
cctgtagcaa tggcaacaac gttgcgcaaa ctattaactg gcgaactact      4756
tactctagct tcccggcaac aattaataga ctggatggag gcggataaag      4806
ttgcaggacc acttctgcgc tcggcccttc cggctggctg gtttattgct      4856
gataaatctg gagccggtga gcgtgggtct cgcggtatca ttgcagcact      4906
ggggccagat ggtaagccct cccgtatcgt agttatctac acgacgggga      4956
gtcaggcaac tatggatgaa cgaaatagac agatcgctga ataggtgcc      5006
tcactgatta agcattggta actgtcagac caagtttact catatatact      5056
ttagattgat ttaaaacttc atttttaatt taaaaggatc taggtgaaga      5106
tcctttttga taatctcatg accaaaatcc cttaacgtga gttttcgttc      5156
cactgagcgt cagacccgt agaaaagatc aaaggatgtt cttgagatcc       5206
ttttttttctg cacgtaatct gctgcttgca acaaaaaaac caccgctacc      5256
agcggtggtt tgtttgccgg atcaagagct accaactctt tttccgaagg      5306
```

```
taactggctt cagcagagcg cagataccaa atactgtcct tctagtgtag      5356
ccgtagttag gccaccactt caagaactct gtagcaccgc ctacatacct      5406
cgctctgcta atcctgttac cagtggctgc tgccagtggc gataagtcgt      5456
gtcttaccgg gttggactca agacgatagt taccggataa ggcgcagcgg      5506
tcgggctgaa cggggggttc gtgcacacag cccagcttgg agcgaacgac      5556
ctacaccgaa ctgagatacc tacagcgtga gctatgagaa agcgccacgc      5606
ttcccgaagg gagaaaggcg gacaggtatc cggtaagcgg cagggtcgga      5656
acaggagagc gcacgaggga gcttccaggg ggaaacgcct ggtatcttta      5706
tagtcctgtc gggtttcgcc acctctgact tgagcgtcga ttttttgtgat     5756 gctcgtcagg ggggcggagc ctatggaaaa acgccagcaa cgcggccttt     5806
ttacggttcc tggccttttg ctggccttt gctcacatgt tctttcctgc      5856
gttatcccct gattctgtgg ataaccgtat taccgccttt gagtgagctg     5906
ataccgctcg ccgcagccga acgaccgagc gcagcgagtc agtgagcgag     5956
gaagcggaag agcgcccaat acgcaaaccg cctctccccg cgcgttggcc     6006
gattcattaa tgcaggtatc acgaggccct ttcgtcttca c              6047
```

FUSION PROTEINS OF HUMANIZED G250 SPECIFIC ANTIBODIES AND USES THEREOF

FIELD OF THE INVENTION

This invention relates to the field of molecular immunology, generally, and to vectors useful for expression of proteins, especially antibodies, such as fully human, humanized, and chimeric antibodies, as well as fusion proteins which incorporate the antibody and a protein or protein fragment, in eukaryotic cells, mammalian cells in particular. The resulting antibodies and fusion proteins are also a feature of the invention.

BACKGROUND AND PRIOR ART

One serious problem with using murine antibodies for therapeutic applications in humans is that they quickly raise a human anti-mouse response (HAMA) which reduces the efficacy of the antibody in patients, and prevents continued administration thereof. Parallel issues arise with the administration of antibodies from other, non-human species. One approach to overcoming this problem is to generate so-called "chimeric" antibodies. These can comprise murine variable regions, and human constant regions (Boulianne et al. (1984) Nature 312(5995): 643-646.; incorporated by reference herein in its entirety). Although chimeric antibodies contain murine sequences and can elicit an anti-mouse response in humans (LoBuglio et al. (1989) Proc. Natl. Acad. Sci. USA 86(11): 4220-4224; incorporated by reference herein in its entirety), trials with chimeric antibodies in the area of hematological disease (e.g., Non-Hodgkin-Lymphoma; Witzig et al. (1999) J. Clin. Oncol. 17(12): 3793-3803.; incorporated by reference herein in its entirety) or autoimmune disease (e.g., rheumatoid arthritis, chronic inflammatory bowel disease; Van den Bosch; et al, Lancet 356(9244):1821-2 (2000), incorporated by reference herein in its entirety) have led to FDA approval and demonstrate that these molecules have significant clinical potential and efficacy.

Recent studies have indicated that granulocyte-macrophage colony stimulating growth factor (GM-CSF) plays a role in the development of rheumatoid arthritis (RA) (Cook, et al., Arthritis Res. 2001, 3:293-298, incorporated by reference herein in its entirety) and possibly other inflammatory diseases and conditions. Therefore, it would be of interest to develop a drug which would block GM-CSF and its effect on cells. The present invention provides a chimeric antibody, targeting the GM-CSF molecule, which has blocking capacity.

The increased use of chimeric antibodies in therapeutic applications has created the need for expression vectors that effectively and efficiently produce high yields of functional chimeric antibodies in eukaryotic cells, such as mammalian cells, which are preferred for production. The present invention provides novel expression vectors, transformed host cells and methods for producing chimeric antibodies in mammalian cells, as well as the antibodies themselves and fusion proteins containing them.

BRIEF DESCRIPTION OF THE FIGURES

FIG. 5 shows results of an assay testing the effect of increasing concentration of murine or chimeric 19/2 mAbs, on TF-1 cells grown in the presence of a constant amount of human GM-CSF.

FIG. 6 parallels the experiment of FIG. 5, but uses the AML-153 cells.

FIG. 7 shows a schematic map of the two expression vectors used to prepare the recombinant antibodies.

SUMMARY OF INVENTION

Figure 1:
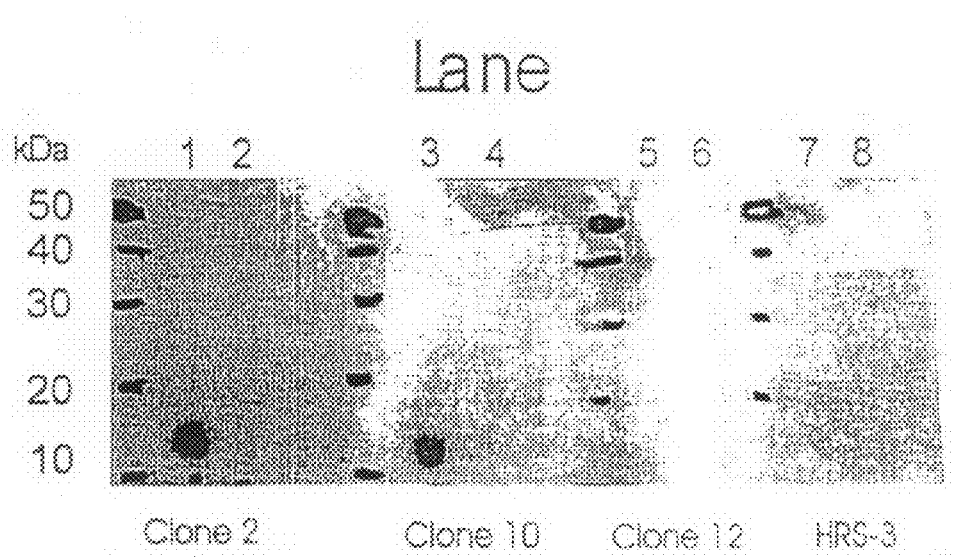
FIG. 1 shows the binding of recombinant, chimeric anti GM-CSF antibody via Western Blotting.

The present invention provides expression vectors which are useful in the expression of proteins, such as antibodies, especially fully human, humanized or chimerized antibodies, and fusion proteins containing these. Both light chains and heavy chains can be expressed. The expression vectors of the present invention comprise a human elongation factor 1 α (EF1α) promoter/enhancer sequence, an internal ribosome entry site (IRES) sequence (U.S. Pat. No. 4,937,190; incorporated herein in its entirety), a nucleotide sequence that confers neomycin resistance to a cell containing the expression vector, and a nucleotide sequence under control of a simian virus 40 promoter (SV40) that confers ampicillin resistance to a cell containing the expression vector. In a preferred embodiment, the EF1α promoter/enhancer sequence is upstream and adjacent to a nucleotide sequence encoding a chimeric light chain.

The expression vector of the present invention may contain a nucleotide sequence encoding any immunoglobulin light chain. In a preferred embodiment the light chain variable region is of murine origin, and the light chain constant region is either human kappa or human lambda. In a more preferred embodiment, the chimeric light chain variable region is derived from a murine antibody that binds to GM-CSF, CD-30, or G250 and in especially preferred embodiments, to the human forms of these molecules.

The present invention also provides a further expression vector useful in the expression of proteins, such as antibodies, especially fully human, humanized or chimeric antibodies, and fusion proteins containing these. This second embodiment differs from the first in that instead of the neomycin resistance sequence, described supra, it comprises a nucleotide sequence which encodes dihydrofolate reductase or "dhfr," which generates resistance against the well known selection marker methotrexate. Such an expression vector may contain nucleotide sequences encoding any antibody or portion thereof, such as heavy or light chains of fully human, humanized or chimerized antibodies. In a preferred embodiment, a heavy chain is expressed, where the variable region is of murine origin, and the heavy chain constant region is human IgG1. In a more preferred embodiment, the chimeric heavy chain variable region is derived from a murine antibody that binds CD-30, GM-CSF or G250, preferably the human forms of these.

In another embodiment, the present invention provides host cells transformed or transfected with any one of the expression vectors of the present invention. In a preferred embodiment, a host cell, preferably a eukaryotic cell, more preferably a mammalian cell, is transformed or transfected with an expression vector comprising a chimeric immunoglobulin light chain and an expression vector comprising a chimeric immunoglobulin heavy chain. The present invention contemplates prokaryotic and eukaryotic cells, such as mammalian cells, insect cells, bacterial or fungal cells. In a preferred embodiment, the host cell is a human or Chinese Hamster Ovary ("CHO") cell.

The present invention also provides methods for the recombinant production of a chimeric immunoglobulin light or heavy chain comprising the step of culturing a transformed or transfected host cell of the present invention. In one embodiment, the methods of the present invention further comprise the isolation of the chimeric immunoglobulin light or heavy chain.

The present invention also provides methods for the recombinant production of a fully human, humanized or chimeric immunoglobulin comprising culturing a host cell that has been transformed or transfected with an expression vector comprising a chimeric immunoglobulin light chain and an expression vector comprising a chimeric immunoglobulin heavy chain, or an expression vector encodes both chains. In one embodiment, the methods of the present invention further comprise the self-assembly of the chimeric heavy and light chain immunoglobulins and isolation of the chimeric immunoglobulin. Methods for accomplishing this are well known in the art.

The present invention also provides the chimeric immunoglobulin light chain, heavy chain or assembled chimeric immunoglobulin produced by the methods of the present invention. In another embodiment, the present invention provides compositions comprising the chimeric immunoglobulin light chain, heavy chain or assembled chimeric immunoglobulin of the present invention and a pharmaceutically acceptable carrier.

DETAILED DESCRIPTION OF INVENTION

1. Definitions

As used herein "chimerized" refers to an immunoglobulin such as an antibody, wherein the heavy and light chains of the variable regions are not of human origin and wherein the constant regions of the heavy and light chains are of human origin.

"Humanized" refers to an immunoglobulin such as an antibody, wherein the amino acids directly involved in antigen binding, the so-called complementary determining regions (CDR), of the heavy and light chains are not of human origin, while the rest of the immunoglobulin molecule, the so-called framework regions of the variable heavy and light chains, and the constant regions of the heavy and light chains are of human origin.

"Fully human" refers to an immunoglobulin, such as an antibody, where the whole molecule is of human origin or consists of an amino acid sequence identical to a human form of the antibody.

"Immunoglobulin" or "antibody" refers to any member of a group of glycoproteins occurring in higher mammals that are major components of the immune system. As used herein, "immunoglobulins" and "antibodies" comprise four polypeptide chains-two identical light chains and two identical heavy chains that are linked together by disulfide bonds. An immunoglobulin molecule includes antigen binding domains, which each include the light chains and the end-terminal portion of the heavy chain, and the Fc region, which is necessary for a variety of functions, such as complement fixation. There are five classes of immunoglobulins wherein the primary structure of the heavy chain, in the Fc region, determines the immunoglobulin class. Specifically, the alpha, delta, epsilon, gamma, and mu chains correspond to IgA, IgD, IgE, IgG and IgM, respectively. As used herein "immunoglobulin" or "antibody" includes all subclasses of alpha, delta, epsilon, gamma, and mu and also refers to any natural (e.g., IgA and IgM) or synthetic multimers of the four-chain immunoglobulin structure.

"Antigen-binding fragment", "antigen-binding domain" and "Fab fragment" all refer to the about 45 kDa fragment obtained by papain digestion of an immunoglobulin molecule and consists of one intact light chain linked by a disulfide bond to the N-terminal portion of the contiguous heavy chain. As used herein, "F(ab)$_2$ fragment" refers to the about 90 kDa protein produced by pepsin hydrolysis of an immunoglobulin molecule. It consists of the N-terminal pepsin cleavage product and contains both antigen binding fragments of a divalent immunoglobulin, such as IgD, IgE, and IgG. Neither the "antigen-binding fragment" nor "F(ab)$_2$ fragment" contain the about 50 kDa $F_c$ fragment produced by papain digestion of an immunoglobulin molecule that contains the C-terminal halves of the immunoglobulin heavy chains, which are linked by two disulfide bonds, and contain sites necessary for compliment fixation.

"Epitope" refers to an immunological determinant of an antigen that serves as an antibody-binding site. Epitopes can be structural or conformational.

"Hybridoma" refers to the product of a cell-fusion between a cultured neoplastic lymphocyte and a normal, primed B- or T-lymphocyte, which expresses the specific immune potential of the parent cell.

"Heavy chain" refers to the longer & heavier of the two types of polypeptide chain in immunoglobulin molecules that contain the antigenic determinants that differentiate the various Ig classes, e.g., IgA, IgD, IgE, IgG, IgM, and the domains necessary for complement fixation, placental transfer, mucosal secretion, and interaction with $F_c$ receptors.

"Light chain" refers to the shorter & lighter of the two types of polypeptide chain in an Ig molecule of any class. Light chains, like heavy chains, comprise variable and constant regions.

"Heavy chain variable region" refers to the amino-terminal domain of the heavy chain that is involved in antigen binding and combines with the light chain variable region to form the antigen-binding domain of the immunoglobulin.

"Heavy chain constant region" refers to one of the three heavy chain domains that are carboxy-terminal portions of the heavy chain.

"Light chain variable region" refers to the amino-terminal domain of the light chain and is involved in antigen binding and combines with the heavy chain to form the antigen-binding region.

"Light chain constant region" refers to the one constant domain of each light chain. The light chain constant region consists of either kappa or lambda chains.

"Murine anti-human-GM-CSF 19/2 antibody" refers to a murine monoclonal antibody that is specific for human GM-CSF. This antibody is well known and it has been studied in detail. See Dempsey, et al, Hybridoma 9:545-58 (1990); Nice, et al, Growth Factors 3:159-169 (1990), both incorporated by reference.

"Effective amount" refers to an amount necessary to produce a desired effect.

"Antibody" refers to any glycoprotein of the immunoglobulin family that non-covalently, specifically, and reversibly binds a corresponding antigen.

"Monoclonal antibody" refers to an immunoglobulin produced by a single clone of antibody-producing cells. Unlike polyclonal antiserum, monoclonal antibodies are monospecific (e.g., specific for a single epitope of a single antigen).

"Granulocytes" include neutrophils, eosinophils, and basophils.

"GM-CSF" refers to a family of glycoprotein growth factors that control the production, differentiation, and function of granulocytes and monocytes-macrophages. Exemplary, but by no means the only form of such molecules, can be seen in U.S. Pat. No. 5,602,007, incorporated by reference.

"Inflammatory condition" refers to immune reactions that are either specific or non-specific. For example, a specific reaction is an immune reaction to an antigen. Examples of specific reactions include antibody responses to antigens, such as viruses and allergens, including delayed-type hypersensitivity, including psoriasis, asthma, delayed type hypersensitivity, inflammatory bowel disease, multiple sclerosis, viral pneumonia, bacterial pneumonia, and the like. A non-specific reaction is an inflammatory response that is mediated by leukocytes such as macrophages, eosinophils and neutrophils. Examples of non-specific reactions include the immediate swelling after a bee sting, and the collection of polymorphonuclear (PMN) leukocytes at sites of bacterial infection. Other "inflammatory conditions" within the scope of this invention include, e.g., autoimmune disorders such as psoriasis, rheumatoid arthritis, lupus, post-ischemic leukocyte mediated tissue damage (reperfusion injury), frost-bite injury or shock, acute leukocyte-mediated lung injury (acute respiratory distress syndrome or ARDS), asthma, traumatic shock, septic shock, nephritis, acute and chronic inflammation, and platelet-mediated pathologies such as ateriosclerosis and inappropriate blood clotting.

"Pharmaceutically acceptable carrier" refers to any carrier, solvent, diluent, vehicle, excipient, adjuvant, additive, preservative, and the like, including any combination thereof, that is routinely used in the art.

Physiological saline solution, for example, is a preferred carrier, but other pharmaceutically acceptable carriers are also contemplated by the present invention. The primary solvent in such a carrier may be either aqueous or non-aqueous. The carrier may contain other pharmaceutically acceptable excipients for modifying or maintaining pH, osmolarity, viscosity, clarity, color, sterility, stability, rate of dissolution, and/or odor. Similarly, the carrier may contain still other pharmaceutically acceptable excipients for modifying or maintaining the stability, rate of dissolution, release, or absorption or penetration across the blood-brain barrier.

The fully human, humanized or chimerized antibodies of the present invention may be administered orally, topically, parenterally, rectally or by inhalation spray in dosage unit formulations that contain conventional non-toxic pharmaceutically acceptable carriers, adjuvants and vehicles. As used herein, "parenterally" refers to subcutaneous, intravenous, intramuscular, intrastemal, intrathecal, and intracerebral injection, including infusion techniques.

The fully human, humanized or chimerized antibodies may be administered parenterally in a sterile medium. The antibodies, depending on the vehicle and concentration used, may be suspended or dissolved in the vehicle. Advantageously, adjuvants such as local anesthetics, preservatives and buffering agents can be dissolved in the vehicle. The most preferred routes of administration of the pharmaceutical compositions of the invention are subcutaneous, intramuscular, intrathecal or intracerebral administration. Other embodiments of the present invention encompass administration of the composition in combination with one or more agents that are usually and customarily used to formulate dosages for parenteral administration in either unit dose or multi-dose form, or for direct infusion.

Active ingredient may be combined with the carrier materials in amounts necessary to produce single dosage forms. The amount of the active ingredient will vary, depending upon the type of antibody used, the host treated, the particular mode of administration, and the condition from which the subject suffers. Preferably, the amount of fully human, humanized or chimerized anti-GM-CSF immunoglobulin, for example, is a therapeutically effective amount which is sufficient to decrease an inflammatory response or ameliorate the symptoms of an inflammatory condition. It will be understood by those skilled in the art, however, that specific dosage levels for specific patients will depend upon a variety of factors, including the activity of the specific immunoglobulins utilized, the age, body weight, general health, sex, diet, time of administration, route of administration, and rate of excretion, drug combination and the severity of the particular disease undergoing therapy. Administration of the fully human, humanized or chimerized immunoglobulins of the present invention may require either one or multiple dosings.

Regardless of the manner of administration, however, the specific dose is calculated according to approximate body weight or body surface area of the patient. Further refinement of the dosing calculations necessary to optimize dosing for each of the contemplated formulations is routinely conducted by those of ordinary skill in the art without undue experimentation, especially in view of the dosage information and assays disclosed herein.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Cloning Strategy for 19/2 Heavy (H) and Light (L) Variable (V)-Region Genes

Total RNA from the hybridoma producing murine 19/2 antibody was obtained by standard RNA isolation techniques (Chomczynski et al. (1987) *Anal. Biochem.* 162: 156-159.; incorporated by reference herein in its entirety). First strand cDNA was prepared using a commercially available, first strand cDNA synthesis kit and priming with d(T) 18 for both the heavy and light chains (Renner et al. (1998) *Biotechniques* 24(5): 720-722.; incorporated by reference herein in its entirety). The resulting cDNA was subjected to PCR using combinations of primers for the heavy and light chains. The nucleotide sequences of the 5' primers for the heavy and light chains are shown in Tables 1 and 2 respectively. The 3' primers are shown in Table 3. The light chain primer hybridized within the mouse kappa constant region not far from the V-C junction. The heavy chain 3' primer hybridised within the CH-1 constant region of mouse heavy chain subgroup I not far from the V-CH1 junction.

TABLE 1

| Oligonucleotide primers for the 5' region of Mouse Heavy Variable (MHV) domains. | | |
|---|---|---|
| | | SEQ ID NO: 1 |
| MHV-1: | 5'ATGAAATGCAGCTGGGTCATSTTCTTC 3' | 1 |
| MHV-2: | 5'ATGGGATGGAGCTRATCATSYTCTT 3' | 2 |
| MHV-3: | 5'ATGAAGWTGTGGTTAAACTGGGTTTTT 3' | 3 |
| MHV-4: | 5'ATGRACTTTGWYTCAGCTTGRTTT 3' | 4 |

TABLE 1-continued

Oligonucleotide primers for the 5' region of Mouse Heavy Variable (MHV) domains.

| | | SEQ ID NO: 1 |
|---|---|---|
| MHV-5: | 5'ATGGACTCCAGGCTCAAMAGTTTTCCTT 3' | 5 |
| MHV-6: | 5'ATGGCTGTCYTRGSGCTRCTCTTCTGC 3' | 6 |
| MHV-7: | 5'ATGGRATGGAGCKGGRTCTTMTCTT 3' | 7 |
| MHV-8: | 5'ATGAGAGTGCTGATTCTTTTGTG 3' | 8 |
| MHV-9: | 5'ATGGMTGGGTGTGGAMCTTGCTATTCCTG 3' | 9 |
| MHV-10: | 5'ATGGGCAGACTTACATTCTCATTCCTG 3' | 10 |
| MHV-11: | 5'ATGGATTTTGGGCTGATTTTTTTATTG 3' | 11 |
| MHV-12: | 5'ATGATGGTGTTAAGTCTTCTGTACCTG 3' | 12 |

NB KEY R = A/G, Y = T/C, W = A/T, K = T/G, M = A/C, S = C/G.

TABLE 2

Oligonucleotides primers for the 5' region of Mouse Kappa Variable (MKV) domains.

| | | SEQ ID NO: 1 |
|---|---|---|
| MKV-1: | 5'ATGAAGTTGCCTGTTAGGCTGTTGGTGCTG 3' | 13 |
| MKV-2: | 5'ATGGAGWCAGACACACTCCTGYTATGGGT 3' | 14 |
| MKV-3: | 5'ATGAGTGTGCTCACTCAGGTCCTGGSGTTG 3' | 15 |
| MKV-4: | 5'ATGAGGRCCCCTGCTCAGWTTYTTGGMWTCTTG 3' | 16 |
| MKV-5: | 5'ATGGATTTWCAGGTGCAGATTWTCAGCTTC 3' | 17 |
| MKV-6: | 5'ATGAGGTKCYYTGYTSAGYTYCTGRGG 3' | 18 |
| MKV-7: | 5'ATGGGCWTCAAGATGGAGTCACAKWYYCWGG 3' | 19 |
| MKV-8: | 5'ATGTGGGGAYCTKTTTYCMMTTTTTCAATTG 3' | 20 |
| MKV-9: | 5'ATGGTRTCCWCASCTCAGTTCCTTG 3' | 21 |
| MKV-10: | 5'ATGTATATATGTTTGTTGTCTATTTCT 3' | 22 |
| MKV-11: | 5'ATGGAAGCCCCAGCTCAGCTTCTCTTCC 3' | 23 |
| MKV-12: | 5'ATGAAGTTTCCTTCTCAACTTCTGCTC 3' | 24 |

NB KEY R = A/G, Y = T/C, W = A/T, K = T/G, M = A/C, S = C/G.

TABLE 3

Oligonucleotide primers for the 3' ends of mouse VH and VL genes.

| Light chain (MKC): | 5'TGGATGGTGGGAAGATG 3' | 25 |
|---|---|---|
| Heavy chain (MHG): | 5'CCAGTGGATAGACAGATG 3' | 26 |

Example 2

Ig Sequences Cloned from the 19/2 Murine Hybridoma

Using the cloning strategy described, supra, PCR products for VH and VL of murine 19/2 were cloned using a commercially available product, and art recognized techniques. For the murine 19/2 VL region, PCR products were obtained using the mouse kappa constant region primer and primers MKV2 and MKV7 (SEQ ID NOS: 14 & 19). For the mouse 19/2 VH region, PCR products were obtained using the mouse gamma 1 constant region primer and primers MHV2, MHV5 and MHV7 (SEQ ID NOS: 2, 5 and 7). Extensive DNA sequencing of the cloned V-region inserts revealed two different light chain sequences and 2 different heavy chain sequences. Pseudogenes for heavy and light chain were amplified and were eliminated by standard sequence analyses. A novel immunoglobulin-coding sequence was determined for both the heavy and light chains. This is set forth at SEQ ID NOS: 27, 28, 29 & 30, which present the cDNA and amino acid sequences for the murine 19/2 heavy chain variable region (27 & 28), and the light chain variable region (29 & 30).

Example 3

Mouse 19/2 Heavy Chain Leader Sequence

When comparing the DNA sequence of the leader sequence for 19/2 heavy chain obtained with the primers described supra, with the database, it appeared that the 19/2 HC leader sequence is short (17 amino acids) and unique vis a vis public data bases. Specifically, amino acids 2, 3 and 5 were E, L & M, as compared to S, W & F in the data bases. As compared to the database, hydrophilic amino acids in the N-terminal region were separated by neutral or basic ones, respectively; however, since the influence of these changes on the secretory capability of the leader sequence is unclear, this sequence was unaltered in further experiments.

Example 4

Construction of Mouse-human Chimeric Genes

The chimeric 19/2 antibody was designed to have the mouse 19/2 VL and VH regions linked to human kappa and gamma-1 constant regions, respectively. PCR primers were used to modify the 5'- and 3'- sequences flanking the cDNA sequences coding for the mouse 19/2 VL and VH regions. PCR primers specific for 19/2 light chain V-region were designed using the sequence of the 19/2 light chain V-region gene obtained. These adapted mouse 19/2 variable regions were then subcloned into mammalian cell expression vectors already containing the human kappa (pREN-Neo vector) or the gamma-1 (pREN-DHFR vector) constant regions. The vectors employ parts of the human elongation factor 1α (EF 1α) promoter/enhancer sequence to efficiently transcribe the light and heavy chains. The vectors also contain an IRES sequence following the multiple cloning site to allow for stringent, bicistronic expression and control of the individual selection marker in CHO cells. This pair of vectors was used in all of the recombinant work described herein, i.e., to manufacture all chimeric antibodies. The expression vectors were designed to have the variable regions inserted as PmeI-BamHI DNA fragments. PCR primers were designed to introduce these restrictions sites at the 5'- (PmeI) and 3'- (BamHI)

ends of the cDNAs coding for the V-regions. In addition, the PCR primers were designed to introduce a standard Kozak sequence (Kozak (1987) *Nucleic Acids Res.* 15(20): 8125-8148, incorporated by reference herein in its entirety) at the 5'-ends of both the light and heavy chain cDNAs to allow efficient translation, and to introduce splice donor sites at the 3'-ends of both the light and heavy chain cDNAs for the variable regions to be spliced to the constant regions. The PCR primers used for the construction of the chimeric 19/2 light and heavy chains were as follows: catgtttaaacgccgccac-catgggcttcaagatggagtca (5' end, light chain variable region, SEQ ID NO: 31); agaggatccactcacgtttcagttccacttggtcccag (3'end, SEQ ID NO: 32); catgtttaaacgccgccaccatggagct-gatcatgctcttcct (primer for the 5' end of the heavy chain variable region, SEQ ID NO: 33); and agaggatccactcacctgag-gagactctgagagtggt (primer for the 3' end of the heavy chain variable region, SEQ ID NO: 34). The DNA and amino acid sequences of the mouse 19/2 VL and VH regions were adapted for use from the construction of chimeric 19/2 light and heavy chains. The entire DNA sequences of mouse 19/2 light and heavy chains cloned into the eukaryotic expression vectors pREN-Neo and pREN-DHFR, respectively, are set forth as SEQ ID NO: 35 & 36, with the resulting light and heavy chains resulting in chimerized molecules. Specifically, in SEQ ID NO: 35, nucleotides 1357-1756 encode the murine, light chain sequence, with nucleotides 1763-2206 encoding the human kappa region. Within this sequence (1763-2206), a 120 base pair region constituting an intron and splice acceptor site begins at nucleotide 1886. Within SEQ ID NO: 36, nucleotides 1357-1770 encode the murine 9/2 heavy chain constant sequence with a splice donor site. Nucleotides 1777-2833 encode the human IgG1 constant region. Within this sequence, there is a 60 base pair intron region and splice acceptor site which precedes the coding region.

Example 5

The objective of the experiments described herein was to create stable cell lines expressing chimeric 19/2 (c19/2) anti-human GM-CSF monoclonal antibodies (mAb) in CHO (Chinese hamster ovary) DG44 cells and to test the secreted antibody for its binding properties. To do this, the DHFR negative CHO cell line DG044 was used. See Morris et al. (1990) *Gene* 94(2): 289-294; incorporated by reference herein in its entirety). The CHO cells were cultured in RPMI, supplemented with 10% FCS and Hypoxanthine-Thymidine. DNA for transfection was purified from *E. coli* cells using a commercially available product, and the instructions provided therein. All DNA preparations were examined by restriction enzyme digestion. Sequences of chimeric 19/2 mAb variable regions in their respective vectors were confirmed using an ABI PRISM 310 or LICOR Sequencer.

Vectors encoding heavy and light chains of chimeric 19/2 mAbs were co-transfected simultaneously into CHO DG44 cells growing at log phase, using electroporation (270V, 975 μF). Cells were plated in 10 cm dishes and cultured with standard medium. Twenty-four hours later, medium was harvested and replaced by fresh RPMI medium supplemented with 10% dialyzed FCS and 500 μg/mL geneticin. After the initial phase of cell killing was over (7-10 days), GMP-grade methotrexate was added at a concentration of 5 nM and gradually increased to 100 nM over the following weeks. Out-growing colonies were picked and screened for antibody production.

Example 6

PCR Amplification of Variable Chain DNA

CHO DG44 cells were centrifuged in an Eppendorf microcentrifuge, briefly, at full speed, washed once with PBS, and pelleted once again. Genomic DNA was prepared by ethanol precipitation after SDS lysis and Proteinase K treatment of the cell pellets.

A mixture containing one of the primer pairs described supra, dNTPs, buffer, and Pfu polymerase was used to amplify either the heavy or light chain variable region using genomic DNA as a template using methods well known in the art. The resulting PCR products were digested with the appropriate restriction enzyme and analysed by agarose gel electrophoresis to confirm their identity.

The primer pairs for the light chain were:

```
ttcttgaagt ctggtgatgc tgcc,          (SEQ ID NO:37)
and caagctagcc ctctaagactc ctcccctgtt.   (SEQ ID NO:38)
```

For the light chain and SEQ ID NO: 37 plus

```
gaactcgagt catttacccg gagacaggga gag (SEQ ID NO:39)
``` for the heavy chain.

The undigested heavy chain PCR product had a predicted size of 1200 base pairs, while the light chain PCR product had a predicted size of 800 base pairs. Identity was verified by restriction enzyme digest with BamHI.

Example 7

Dot-Blot Method for Measuring Assembled IgG1/Kappa Antibody in CHO Cell Supernatants CHO cell lines were transfected with the corresponding plasmids. Geneticin resistant cells were obtained and these cells were further selected for resistance to methotrexate. Single colonies were picked after amplification and transferred into 24-well plates. Culture supernatant was tested for chimeric IgG 3-4 days later by standard Dot Blot assays.

Figure 2:
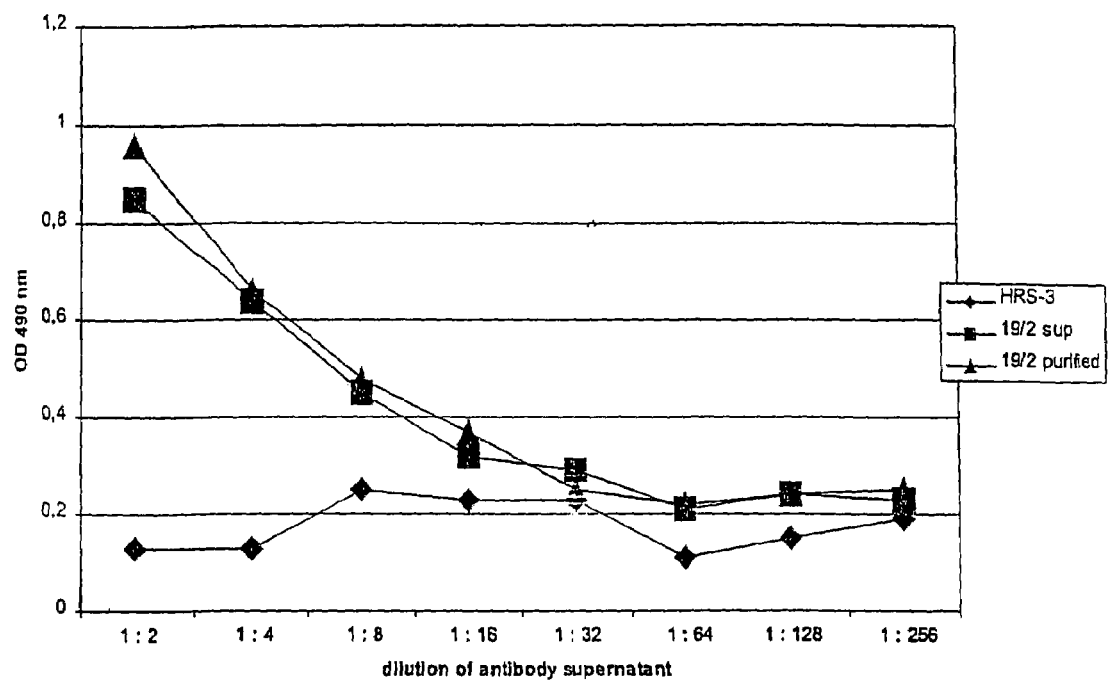
FIG. 2 shows the binding of the antibody via ELISA.

Any positive colonies were sub-cloned and cultured to achieve sufficient antibody production. The chimeric 19/2 antibody was purified from the supernatant on protein G columns and tested for its specific binding with recombinant GM-CSF by Western Blot (FIG. 1) and ELISA (FIG. 2).

Finally, the identity of producer cell lines were confirmed using PCR amplification of both their heavy and light chain variable regions. The DNA sequence of the heavy chain variable region PCR products for chimeric 19/2 mAb transfected cells was confirmed.

Example 8

In order to optimize cell growth and antibody production, the CHODG44/pREN c19/2 cell line was first cultured in commercially available IMDM containing 10% FCS, at 37° C., in a 10% $CO_2$ atmosphere. The cells were then weaned into serum free medium, and cultured in a custom made medium, i.e., IMDM SFII, with the following additives, at 37° C., in a 10% $CO_2$ atmosphere.

| | Final Concentration |
|---|---|
| Base IMDM Medium | |
| Pluronic F68 | 1.0 mg/ml |
| Hypep 4601 | 1.0 mg/ml |
| Hypep 4605 DEV | 0.5 mg/ml |
| HEPES | 5.958 mg/ml |
| $Na_2HCO_3$ | 3.024 mg/ml |
| Additives | |
| Dextran sulfate | 50.0 µg/ml |
| Putrescine | 100.0 nM |
| Albumax I | 2.0 mg/ml |
| Choline chloride | 1.0 mg/ml |
| Trace elements | |
| $FeSO_4.7H_2O$ | 0.8 µg/ml |
| $ZnSO_4.7H_2O$ | 1.0 µg/ml |
| $CuSO_4.5H_2O$ | 0.0025 µg/ml |
| $C_6H_5FeO_7.H_2O$ | 5.0 µg/ml |
| IGF-1 | 50.0 ng/ml |
| Transferrin | 35.0 µg/ml |
| Ethanolamine | 50.0 µM |
| Mercaptoethanol | 50.0 µM |

Culture supernatants were harvested aseptically, and then clarified by centrifugation. The antibodies were then purified by affinity chromatography on a 5 ml protein. A Sepharose® fast flow column that had been pre-equilibriated in 50 mM Tris-HCL, pH8, was used. The column was washed, 20 times, with this buffer, and any bound antibody was eluted using 50 mM sodium citrate, pH 3.0, and the eluate was then neutralized, immediately, using 1M Tris-HCl, pH8. Antibodies were concentrated with a centrifugal filter, and dialyzed overnight at 4° C. in PBS. The yield was about 4-5 mg/liter. The purity of the antibodies was examined via SDS-PAGE, under both reducing and non-reducing conditions, using a 4-20% gradient on the SDS-PAGE.

Purified antibodies migrated as a single band under non-reducing conditions, and separated into the heavy and light chains, as expected, under reducing conditions.

The antibodies were also analyzed via size exclusion chromatography, (0.5 mg/ml), on a precalibrated HPLC column. Running buffer (5% n-propanol/PBS (0.5 M phosphate, 0/25 M NaCl, pH 7.4)) was used, at a flow rate of 0.2 ml/min at a temperature of 22° C., which is ambient column temperature.

The analysis demonstrated the integrity of the antibodies, which had calculated molecular weights of 179 kilodaltons.

Example 9

The experiments described in this example were designed to determine the binding activity of the antibodies.

Biosensor analyses were carried out using a commercially available, Biacore® 2000, and a carboxymethyldetran coated sensor chip. The chip was derivatized with 1000, 300, or 100 RVs of recombinant human GM-CSF, on channels 1, 2, and 3 of the machine using standard amine coupling chemistry with channel 4 retained as the control blank channel.

Samples of the chimeric antibody were diluted in HBS buffer (10 mM HEPES, pH 7.4, 150 mM NaCl, 3.4 mM di-NA-EDTA, 0.005% Tween-20®), and aliquots were injected over the sensor chip at a flow rate of 1 µl/min. After injection, dissociation was monitored by allowing NBS buffer to flow over the chip surface for 5 minutes. Any bound antibody was then eluted, and the chip surface was regenerated, between samples, via injecting 40 µl of 100 mM HCl, pH 2.7, at a rate of 5 µl/min. In order to carry out kinetic analyses of the binding of the chimeric antibody, varying concentrations, ranging from 1-10 nM, were injected over the chip surface, and both apparent association ("Ka") and dissociation ("Kd") rate constants were calculated, using a Langmuir 1:1 binding model, with global and local fitting for calculation of Rmax, using B1 Aevaluation V3.1 software.

The results indicated that the chimeric antibody had slightly higher affinity for rhGM-CSF than the murine antibody. The calculated Ka for the chimeric antibody was $5.1 \times 10^5 M^1 s^{-1}$ using 100 RU of GM-CSF. No dissociation was observed, regardless of analyte concentration, precluding Kd determination and indicating very high affinity.

Global fitting of Rmax, using the software referred to, gave an off rate of $Kd=1.9 \times 10^{-5} s^{-1}$ and a high affinity for the chimeric antibody of $2.69 \times 10^{10} M^{-1}$.

Example 10

These experiments were designed to determine both the binding activity of the antibodies, and if they cross-reacted with each other.

Nunc plates were coated with recombinant human GM-CSF (1 µg/ml), in carbonate buffer (pH 9.6, 0.05 M), 50 µl/well, and were incubated at 4° C., overnight, and were then blocked with 3% FCS/PBS at room temperature, for one hour.

Half-log, serially diluted triplicate 100 µl samples of either murine or chimeric antibody (10 µg/ml) were added to each well, to yield final concentrations of from 1.0 ng/ml to 10 µg/ml. Following incubation for 1 hour at room temperature, either goat antimouse IgG or antihuman IgG, labelled with horseradish peroxidase (10 ul/well Fc specific; 1:1000 dilution in 1% FCS/PBS) were used to detect bound antibody. After extensive washings, the bound antibodies were visualized by the addition of ABTS substrate (100 µl/well).

Optical density was read at 415 nm in a microplate reader.

The same protocol for binding antibody to the solid phase was used to determine if the antibodies competed with each other. As in the experiments, supra, half-log, serially diluted 100 µl samples, in triplicate, of 10 µg/ml of the murine or chimeric antibody were combined with 20 µg/ml of competing antibody, and then 100 ml of the mixture was added to the coated ELISA plates. Incubation was as above, and anti-murine or anti-human IgG labelled with horseradish peroxidase was used, also as described supra.

The results indicated that the antibodies did compete for binding for recombinant human GM-CSF. A shift in the binding curve was effected by addition of the excess, competing antibody. This indicated binding to, and competition for, a common epitope.

Example 11

These experiments were designed to test the neutralizing activity of the anti-GM-CSF antibodies. Two human GM-CSF dependent cell lines, i.e., TF-1 and AML-193 were used. Growth curves were established, in the presence or absence of 0.5 ng/ml of recombinant human GM-CSF, and viable cell numbers were determined, via Trypan Blue exclusion, on day 0, 1, 2, 3, 5 and 7.

In a first bioassay, recombinant human GM-CSF, in amounts ranging from 0.0003 ng/ml up to 10 µg/ml, was mixed with anti-human GM-CSF antibodies, at a final concentration of 30 µg/ml, in 96 well, microtitre plates. Either TF-1 or AML-193 cells were added ($10^3$ cells/well), and plates were incubated at 37° C. for 7 days.

After this incubation period, the DNA proliferation marker MTS was added, at 20 µl/well. Dye incorporation was measured after 2 hours, by measuring light absorbance at $A_{490nm}$.

Increased MTS dye incorporation was observed as the amount of rhGM-CSF in the medium increased. Total growth inhibition of both cell types was observed with the chimeric antibody when rhGM-CSF concentration was 0.1 ng/ml or less, and there was marked inhibition of cell growth at 0.3-10 ng/ml rhGM-CSF.

Figure 3:
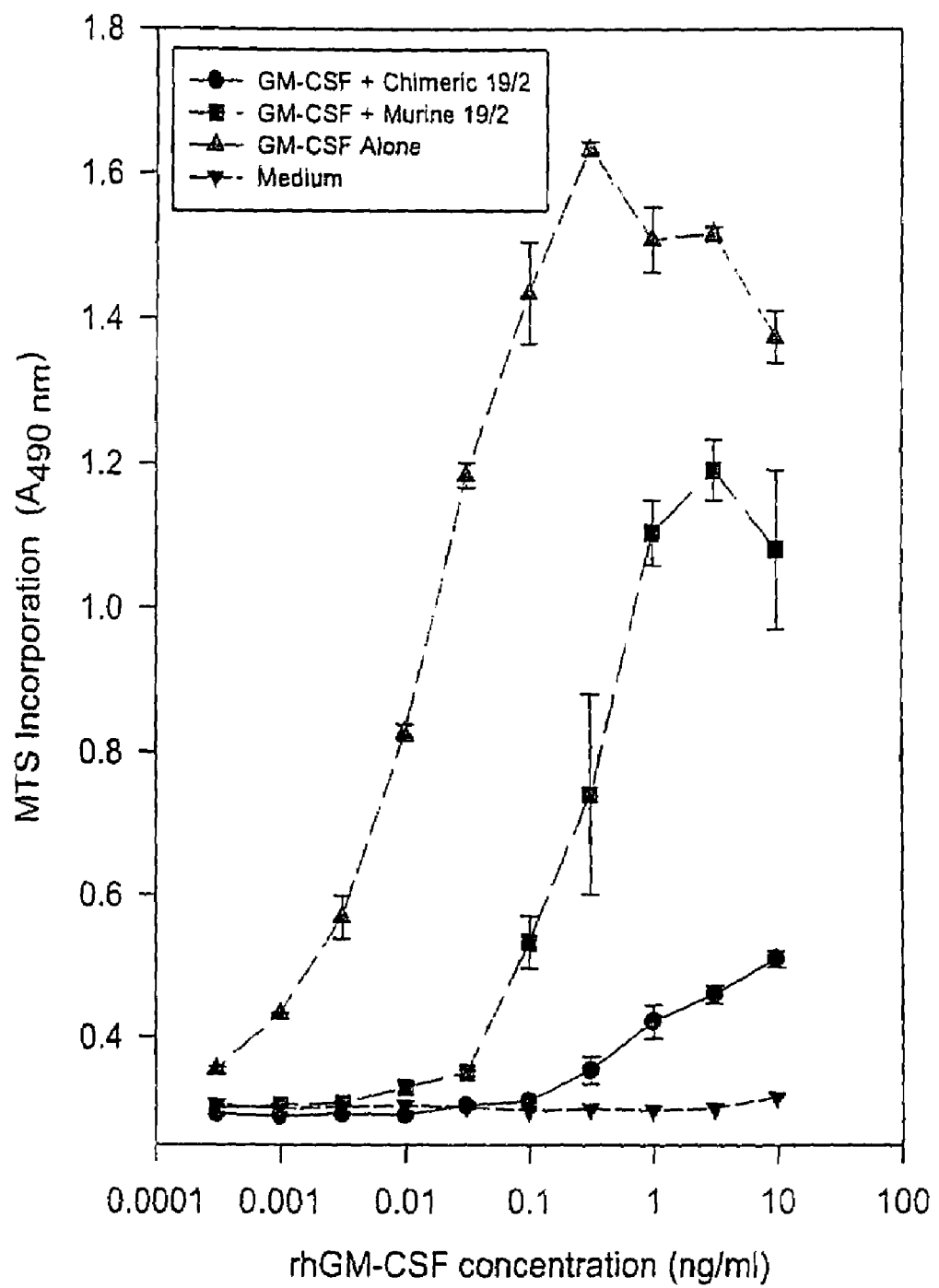
FIG. 3 shows the blocking effect of the antibody on GM-CSF growth dependent TF-1 cells.
Figure 4:
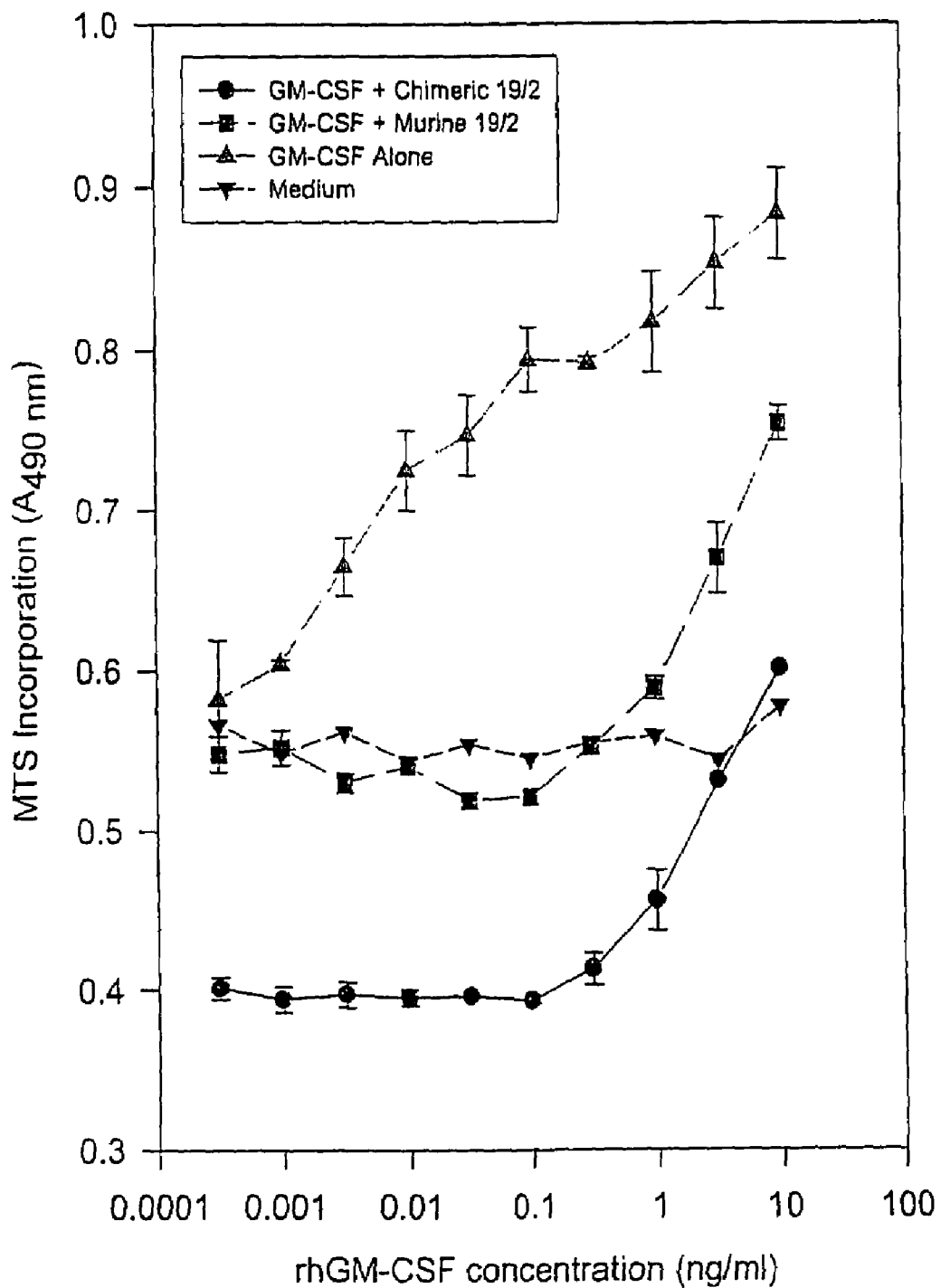
FIG. 4 shows the blocking effect of the antibody on GM-CSF growth dependent AML-193 cells.

In contrast, while the murine antibody had a similar effect on AML-193 cells, it was less effective on TF-1 cells. These results are seen in FIGS. 3 and 4.

In a second bioassay TF-1 and AML-193 cells were grown in the presence of 0.5 ng/mL rhGM-CSF and increasing amounts of murine or chimeric 19/2 mAbs (0.003-100 µg/mL) were added to the culture media and the neutralizing activity assessed after 7 days culture. Results are shown in FIGS. 5 and 6 for the TF-1 and AML-193 cells, respectively. In agreement with the initial bioassay, the chimeric 19/2 demonstrated marked neutralizing activity of GM-CSF stimulated cell growth. A direct correlation was observed between increasing ch19/2 concentration and GM-CSF neutralizing activity plateaued at 3 µg/mL for both cell lines, with higher concentrations unable to effect a greater reduction in TF-1 or AML-193 cell growth. These observations may be due to lower affinity of the murine mAb or steric hindrance at the binding site on GM-CSF.

Example 12

Additional experiments were carried out to produce a chimeric, HRS-3 antibody. The murine form of this antibody is described by Hombach, et al, Int. J. Cancer 55:830-836 (1993), incorporated by reference. The murine antibody binds to CD-30 molecules.

The protocols set forth for production of chimeric, anti GM-CSF antibody set forth supra were used. Since the antibodies were different, and sequences were known, however, different primers were used. These primers serve to introduce splice sites into the cDNA sequences encoding the murine heavy chain and light chain variable regions, and are set forth at SEQ ID NOS: 44, 45, 46 & 47, with SEQ ID NOS: 44 & 45 the nucleotide and amino acid sequences of the heavy chain, and 46 & 47 comparable sequences for the light chain The primers were:

```
                                      (SEQ ID NO:40)
gcgccatggc ccaggtgcaa ctgcagcagt ca
and (SEQ ID NO:41)
cagggatcca ctcacctgag gagacggtga ccgt,
``` and for the light chain:

```
                                      (SEQ ID NO: 42)
agcgccatgg acatcgagct cactcagtct cca
and (SEQ ID NO: 43)
cagggatcca actcacgtttg atttccagct tggt.
```

Following amplification, the murine heavy and light chain variable regions were cloned into the pREN Neo and pREN-DHFR sequences, which are set forth at SEQ ID NOS: 48 & 49, respectively. The cloning was possible because the amplification introduced PmeI and BamHI restriction sites into SEQ ID NO: 44, at nucleotides 1-7, and the final 6 nucleotides. Comparable sites are found at nucleotides 1340-1348, and 1357-1362 of SEQ ID NO: 48. Similarly, PmeI and BamHI restriction sites were introduced at nucleotides 1-8, and the last 6 nucleotides of SEQ ID NO: 47, such that this nucleotide sequence could be cloned into SEQ ID NO: 49, at positions 1337-1344, and 1349-1354.

The chimeric HRS-3 antibody was designed to have murine HRS-3 VL and VH regions linked to human kappa and gamma-1 constant regions, respectively. PCR primers were used to modify the 5'- and 3'-sequences flanking the cDNA sequences coding for the murine HRS-3 VL and VH regions. Modification included the insertion of a NcoI site at the 5' primer end and a splice donor site followed by a BamHI restriction site at the 3'-end of both the light and heavy chain cDNAs for the variable regions to be spliced to the constant regions. These adapted mouse HRS-3 variable regions were then subcloned through the NcoI/BamHI restriction sites into a prokaryotic vector harboring a 5'PmeI site followed by a 5' Kozak sequence and by a human antibody leader sequence. Sequences were cut from the prokaryotic vector by PmeI/BamHI digest and subcloned into mammalian cell expression vectors already containing the human kappa (pREN-Neo vector) or gamma-1 (pREN-DHFR vector) constant regions, described supra.

Example 13

Once the constructs were established, they were transfected into DGO44 cells, as described supra.

Positive colonies were sub-cloned, cultured to achieve sufficient antibody production, after which the antibodies were purified, on protein G columns via the Fc fragment.

The purified antibodies were analyzed via SDS-PAGE, following Laemmli, Nature 227:680-5 (1970), as modified by Renner, et al, Eur. J. Immunol 25:2027-35 (1995), incorporated by reference. Samples from different stages of purification were diluted, in either reducing or non-reducing buffer, and were separated on 10-12% polyacrylamide gel via electrophoreses followed by standard Coomassic staining.

The results were in accordance with production of a complete, chimeric antibody, as evidenced by the banding patterns found in both reducing and non-reducing solutions.

Example 14

The binding capacity of the chimeric HRS-3 antibody was determined via flow cytometry, in accordance with Renner, et al, supra. In brief, $1\times10^6$ cells of a target tumor line which expressed CD-30 were washed, twice, in PBS, and then incubated with varying concentration of antibody, at 4° C., for 30 minutes. The cells were then washed, and incubated with a secondary antibody, which was directed to the light chain, conjugated to either FITC or PE.

The results indicated that there was weak binding from cell culture supernatant purified from transfected CHO cells, and string binding with purified antibody. No binding was found when CD-30 negative tumor cells were used.

Example 15

The antibody dependent cellular toxicity (ADCC), and the complement dependent toxicity of the chimeric HRS-3 antibody were determined using a europium released assay, as described by Hombach, et al, supra, and Renner, et al, supra.

In brief, for the ADCC assay, peripheral blood lymphocytes were isolated from tow healthy donors, and used at an effector:target ratio of 10:1, with 10,000 europium labelled, CD-30 antigen positive L540CY tumor cells. Antibody was added at varying concentrations (10, 1, 0.1 and 0.01 µg/ml), as was a control of 0 µg/ml. The effect was compared to the murine antibody, a bispecific murine anti-CD16/CD30 antibody, and an irrelevant, chimeric IgG1 antibody. A CD30 negative line was also used. Maximum lysis was measured after 0.025% Triton was added, and all assays were carried out in triplicate.

The results indicated that the chimeric antibody performed better in the ADCC than the murine antibody.

In the CDC assays, 10,000 europium labelled cells (100 µg) (L540Y), were incubated, with 50, 5, 0.5, or 0.05 µg/ml antibody in a 50 µl volume. Freshly isolated complement (50 µl) was added, and the mixture was incubated for 2 hours, at 37° C. The murine antibody was also tested, as was an anti CD-16 antibody and a chimeric anti IgG antibody, which served as controls, as did a CD-30 negative cell.

As in the ADCC assay the chimeric antibody was superior in terms of percent lysis to all other antibodies tested.

Example 16

G250 is an antigen also known as "carbonic anhydrase 9," or "CA9," or "MN." The G250 antigen and the corresponding antibody was described as being associated with renal cancer carcinoma by Oosterwijk, et al, PCT/US88/01511. The G250 antibody has also been the subject of several clinical trials (Oosterwijk, et al., Int. J. Cancer 1986: Oct. 15, 38(4):489-494; Divgi, et al., Clin. Cancer Res. 1998: Nov 4(11):2729-739.

Zavada, et al, have issued a series of patents in which the G250 antigen is referred to as "MN" or "MN/CAIX." See, e.g., U.S. Pat. Nos. 6,051,226; 6,027,887; 5,995,075, and 5,981,711, all of which are incorporated by reference. These parents provide details on the antigen, and describe various tumors in which it is found, including cervical cancer, bladder cancer, mammary carcinoma, uterine, cervical, ovarian, and endometrial cancer.

Recently, Ivanov, et al, Am. Journal of Pathology 158(3): 905-919 (2001), conducted investigations of CA9 and CA12 on tumor cells, and cell lines.

cDNA sequences for the light and heavy variable regions of a murine G250 specific antibody are known, and these include the endogenous antibody leader sequence. PCR primers were used to modify both the 5' and 3' regions, in order to introduce restriction sites necessary for the introduction of the coding sequences to the vectors employed, which were SEQ ID NOS: 48 & 49, supra. The cDNA sequence which encodes the murine G250 heavy chain variable region is set forth at SEQ ID NO: 50, with the amino acid sequence at SEQ ID NO: 51 and the light chain variable region, at SEQ ID NO: 52, with amino acid sequence at SEQ ID NO: 53. The first 8 nucleotides in each of SEQ ID NOS 50 & 52 represent a PmeI restriction site. The first 19 amino acids encoded by the nucleotide sequence represent the leader region, and the first 24 the leader sequence for the light chain. The last 6 nucleotides in each of SEQ ID NOS: 50 & 52 are a BamHI restriction site. The same protocol as was used for the HRS-3 chimera was used to splice these variable regions into SEQ ID NOS: 46 & 47.

To secure the cDNA encoding human TNF, a human leukocyte cDNA library was used. The peripheral blood lymphocytes were stimulated with PMA, and the cDNA for TNF was amplified, using standard methods. Restriction sites were introduced in the cDNA sequence, so that the cDNA for TNF was positioned right after the hinge region of the G250 heavy chain. A (Gly) Ser coding sequence linked the two. SEQ ID NOS: 54 & 55 set forth the nucleotide and amino acid sequences of a TNF fragment, and SEQ ID NO: 56, a construct wherein the human gamma-1 heavy chain is followed by the TNF coding sequence, right after the IgG1 hinge region.

Within SEQ ID NO: 56, nucleotides 1419-1754 encode a partial, human IgG1 constant region, containing the CH1 and hinge domain, preceded by a 60 base pair intron region and splice acceptor site. The linker, i.e., $(Gly)_4Ser$ is encoded by nucleotides 1755-1769. The coding sequence for the human TNF fragment is set forth at nucleotides 1776-2296.

The resulting constructs were transfected into host cells, as described supra, and expressed. Note that SEQ ID NO: 56 contains a variant of the heavy chain vector noted supra, as it contains the human CH1 and hinge regions, followed by the TNF encoding sequence.

Cells were transfected and cultured as described supra for the HRS-3 chimera, and amplification was carried out using the primers of SEQ ID NOS: 40-43, described supra. The predicted size of the amplification product was 1100 base pairs, and this was in fact confirmed.

Positive colonies were then sub-cloned and cultured, as described supra. The chimeric G250-TNF fusion proteins were purified using anion exchanged chromatography on DEAE columns, using 5 ml samples, and increased salt concentrations in the elution buffer (NaCl, 0→0.5 M) (pH 8). The purity of the fusion proteins was determined, on SDS-PAGE, under reducing conditions. Two bands, of 45 and 28 kDa, respectively, appeared, consistent with the production of a chimeric fusion protein.

The purity of the chimeric fusion protein was confirmed in a sandwich ELISA. In brief, plates were coated with 1:6000 dilutions of affinity purified, goat anti-human IgG serum, and incubated overnight. They were then blocked with 2% gelatin. Either cell culture supernatant, or purified antibody was added, at varying concentrations, and then contacted with biotinylated goat anti-human TNFα specific serum, at 0.1 µg/ml, followed by visualization with a standard streptavidin peroxidase reagent.

The ELISA confirmed the purity of the antibody.

Example 17

FACS was carried out, as described supra for the chimeric HRS-3 antibodies, this time using the fusion protein, and G250 positive tumor cells. Two different purification runs were tested, with chimeric G250 antibody as a positive control, and an irrelevant chimeric IgG1 antibody as a negative control.

The results indicated that the chimeric fusion protein bound as well as the chimeric antibody did. No binding was detected when G250 negative cells were used.

Example 18

These experiments were designed to determine if the fusion proteins retained the ability of TNF to mediate cell death.

This was accomplished using an MTT assay as described by Renner, et al, Eur. J. Immunol 25:2027-2035 (1995), incorporated by reference, and TNF sensitive ("WEHI-R") cells. The WEHI cells were seeded at a density of 10,000 cells/well. Then, after 18 hours, sterile samples of the fusion protein, recombinant TNF, chimeric G250 antibody, or a negative control (plain medium), were added, at concentrations of 1.0×10⁵, 1.0×10², 1, 1.0×10⁻², 1.0×10⁻⁴, and 1.0×10⁻⁵ ng/ml, and the culture was incubated for additional period of from 48-72 hours. Any viable cells were detected, via standard methods, including Annexin V staining, and flow cytometry. To do this, 1×10⁶ WEHI cells were incubated, overnight, with varying antibody concentrations, and dye positive cells were counted. The effect of antibody loaded tumor cells in WEHI killing was determined by pre-staining with commercially available PKH-26GL dye.

The chimeric fusion proteins were found to be as effective as recombinant TNF in killing cells.

Example 19

It is known that TNF stimulates $H_2O_2$ release by human leukocytes. The chimeric fusion proteins were tested for this property.

Granulocytes were isolated from blood samples via standard methods, and were resuspended in reaction buffer (KRPG=145 mM NaCl, 5 mM $Na_2HPO_4$, 4.8 mM KCl, 0.5 mM $CaCl_2$, 1.2 mM $MgSO_4$, 0.2 mM glucose, pH 7.35). This mix was added plates that had been precoated with fibronectin (1 µg/ml, 2 hours, 37° C.) to permit granulocyte adherence. Following this, 100 11 of a dye solution (10 ml KRPG+50 µl A6550+10 µl horseradish-peroxidase) were added and incubated for 15 minutes at 37° C. Granulocytes were added, at 30,000 cells per well, and then either buffer (KRPG), PMA (5 ng/ml), the chimeric fusion protein (1 µg/ml) plus recombinant human IFN-γ (100 µ/ml), or the fusion protein plus the recombinant IFN-γ (at the indicated concentrations), were added. $H_2O_2$ release was measured for 3 hours, using standard methods.

The PMA served as a positive control. The chimeric fusion protein induced $H_2O_2$ release significantly higher than antibody alone, and the $H_2O_2$ release increases even more when IFN-γ was added.

We claim:

1. A recombinant antibody which specifically binds to renal cell carcinoma associated antigen G250, wherein said recombinant antibody comprises a light chain polypeptide of an antibody that specifically binds to renal cell carcinoma associated antigen G250 and a fusion protein comprising a portion of a heavy chain polypeptide of said antibody that specifically binds to renal cell carcinoma associated antigen G250 adjoined via a linker peptide to a fragment of tumor necrosis factor (TNF) consisting of the amino acid sequence encoded by SEQ ID NO: 56 from nucleotide position 1776 to nucleotide position 2296, wherein said portion consists of the variable domain, the CH1 domain, and the hinge region of said heavy chain polypeptide.

2. An isolated nucleic acid which encodes the recombinant antibody of claim 1.

3. An expression vector comprising the isolated nucleic acid molecule of claim 2 operably linked to a promoter.

4. The expression vector of claim 3, wherein the heavy chain variable domain of said heavy chain polypeptide is encoded by SEQ ID NO:50.

5. An isolated recombinant cell comprising the isolated nucleic acid molecule of claim 2.

6. An isolated recombinant cell comprising the expression vector of claim 3.

7. The recombinant cell of claim 5 wherein said cell is mammalian.

8. The recombinant cell of claim 6 wherein said cell is mammalian.

9. The recombinant cell of claim 8 wherein said cell is a chinese hamster ovary cell.

* * * * *